(12) United States Patent
Thornton et al.

(10) Patent No.: US 9,267,895 B2
(45) Date of Patent: Feb. 23, 2016

(54) CHEMICAL ANALYSIS DEVICE

(71) Applicants: The University of Tokyo, Tokyo (JP); Kyoto University, Kyoto (JP); OK Lab. Co. Ltd., Tokyo (JP)

(72) Inventors: Blair Thornton, Tokyo (JP); Tetsuo Sakka, Kyoto (JP); Koichi Oki, Tokyo (JP)

(73) Assignees: THE UNIVERSITY OF TOKYO, Tokyo (JP); KYOTO UNIVERSITY, Kyoto-Shi, Kyoto (JP); OK LAB. CO. LTD., Mitaka-Shi, Tokyo (JP)

( * ) Notice: Subject to any disclaimer, the term of this patent is extended or adjusted under 35 U.S.C. 154(b) by 0 days.

(21) Appl. No.: 14/427,735

(22) PCT Filed: Sep. 12, 2013

(86) PCT No.: PCT/JP2013/074729
§ 371 (c)(1),
(2) Date: Jun. 1, 2015

(87) PCT Pub. No.: WO2014/042221
PCT Pub. Date: Mar. 20, 2014

(65) Prior Publication Data
US 2015/0268168 A1  Sep. 24, 2015

(30) Foreign Application Priority Data

Sep. 13, 2012 (JP) ................. 2012-201421

(51) Int. Cl.
*G01J 3/30* (2006.01)
*G01N 21/71* (2006.01)

(52) U.S. Cl.
CPC ...... *G01N 21/718* (2013.01); *G01N 2201/0612* (2013.01); *G01N 2201/0833* (2013.01)

(58) Field of Classification Search
CPC .............. G01N 21/718; G01N 21/645; G01N 21/6458; G01J 3/02; G01J 3/4406
USPC .................................. 356/300–445
See application file for complete search history.

(56) References Cited

U.S. PATENT DOCUMENTS 6,100,526 A    8/2000  Mayes
7,530,265 B2   5/2009  DiFoggio
(Continued)

FOREIGN PATENT DOCUMENTS

JP    H03-002884 Y2   1/1991
JP    2614765 B2      5/1997
(Continued)

OTHER PUBLICATIONS

PCT, "International Search Report for International Application No. PCT/JP2013/074729." Jan. 14, 2014.
(Continued)

*Primary Examiner* — Abdullahi Nur
(74) *Attorney, Agent, or Firm* — Manabu Kanesaka

(57) ABSTRACT

Provided is a chemical analysis device to analyze a chemical composition of a sample, including a main body including a laser light source, a chemical analysis unit, and a housing; an optical head that is arranged to be faced to the sample; and a pressureproof-feedthrough-equipped fiber that is extended from the housing to the optical head to guide laser light emitted from the laser light source to the optical head. The housing houses the laser light source and the chemical analysis unit as having a pressure-resistant function. The optical head includes a mirror system that causes the sample to be irradiated with laser light outgoing from the pressureproof-feedthrough-equipped fiber and to cause plasma emission light occurring at the sample owing to irradiation with the laser light to reenter to the pressureproof-feedthrough-equipped fiber. The chemical analysis unit performs spectroscopic analysis on the plasma emission light that reentered to the pressureproof-feedthrough-equipped fiber.

6 Claims, 21 Drawing Sheets

(56) References Cited

U.S. PATENT DOCUMENTS

| | | | |
|---|---|---|---|
| 8,202,478 B2 | 6/2012 | Oguri | |
| 2006/0043301 A1* | 3/2006 | Mantele | G01N 21/3577 250/339.11 |

FOREIGN PATENT DOCUMENTS

| | | |
|---|---|---|
| JP | 2000-338264 A | 12/2000 |
| JP | 2003-526079 A | 9/2003 |
| JP | 2004-028824 A | 1/2004 |
| JP | 2005-140529 A | 6/2005 |
| JP | 2009-510439 A | 3/2009 |
| JP | 2009-097976 A | 5/2009 |
| JP | 2009-236902 A | 10/2009 |

OTHER PUBLICATIONS

Sakka, Tetsuo et al., "Development of In Situ Elemental Analysis Technique for the Water Environment of Lake Biwa," Sustainability Science Research Unit, 2010, p. 117-120.

Taffe, A. et al., "Development of a portable LIBS-device for quality assurance in concrete repair," Concrete Repair, Rehabilitation and Retrofitting II, 2009, p. 547-549, Taylor & Francis Group, London.

* cited by examiner

Seawater

CHEMICAL ANALYSIS DEVICE

RELATED APPLICATIONS

The present application is National Phase of International Application No. PCT/JP2013/074729 filed Sep. 12, 2013, and claims priority from Japanese Application No. 2012-201421, filed Sep. 13, 2012, the disclosure of which is hereby incorporated by reference herein in its entirety.

TECHNICAL FIELD

The present invention relates to a chemical analysis device that enables to perform chemical analysis more effectively in underwater environment especially at a sea bed, a lake bed, or a river bed.

BACKGROUND ART

The surface of the earth is covered with water at 70% or more thereof. Therefore, our life is closely related to underwater environment. To comprehend problems relating to energy resources, mineral resources capable of being used and environment pollution, it is important to perform investigation at a sea bed, a lake bed, and a river bed.

It has been required in many fields to analyze the chemical composition of water and solid material in water. Currently, a sample is taken from an investigation area and chemical analysis of the sample is performed on land. However, such method is time-consuming and costly and analysis results cannot be obtained in real time. Further, there may be a risk that impurities are mixed to a sample when the sample is taken out of water onto land.

Considering the above, it is required to perform investigation in water. However, such investigation in water is associated with difficulties for the following reasons.
[Difficulty 1]
Since water pressure is high in deepwater environment, water-resistant and pressure-resistant properties are required. Further, owing to high water pressure, physical conditions in deepwater environment is different from that on land. Accordingly, there arises a case that a measurement method and device specifications in deepwater environment are required to be varied from those on land.
[Difficulty 2]
Since areas where people can directly perform investigation are limited in water, it is required in many cases to perform investigation using a submersible. Here, it is required that operations of devices and equipment and collection of information can be performed with remote control or direct robot action.
[Difficulty 3]
Since radio waves cannot travel far in underwater environment such as at a sea bed, cables or sound waves are to be adopted as communication tools. Accordingly, it is required that operations, measurement, and data collection can be performed within an investigation device in a self-sustaining manner to some extent.

Conventionally, in general, chemical analysis of a sample has been performed on land using a mass analyzer and the like after water, deposition substances or rocks in water and the like are taken as the sample. On land, since chemical analysis with high accuracy such as inductively coupled plasma (IPC) emission spectroscopic analysis and mass analysis can be performed, chemical analysis of a sample can be performed in detail.

However, to take a sample onto land, an area for investigation is limited. Further, it is time-consuming and costly. In addition, since the chemical composition of a sample are unknown at the time when the sample is taken, information feedback thereof cannot be provided to an investigation plan. Therefore, it is difficult to effectively perform investigation. Furthermore, there may be a risk that impurities are mixed to a sample when the sample is taken onto land.

In view of the above, as an analysis technology substituting as the sampling method, there has been proposed a device capable of performing on-site measurement of a multi-element analysis of chemicals contained in liquid such as water and in solid material in liquid using a method of laser induced breakdown spectroscopy (LIBS).

Chemical analysis using the LIBS has advantages described below. As being based on emission spectroscopic analysis, it is possible to simultaneously detect a plurality of elements. Further, since liquid and solid material can be directly analyzed, pretreatment of a sample is not required to be performed. Further, analysis measurement equipment can be compactified. Thus, a great advantage of the LIBS is that chemical analysis can be performed on site even for investigation in water. However, in underwater environment being at a sea bed, a lake bed, or a river bed, there have been a number of problems of being incapable of measuring unless factors of the difficulties in underwater investigation are overcome.

FIG. 1 illustrates a conventionally typical LIBS analysis device (devise based on Non-Patent Document 1 described below).

A laser beam emitted from a pulse laser 1 (with a beam emission time of the pulse laser being about 10 nsec) passes through a half mirror 7, is collected by a collecting lens 8, and passes through a window 9. Thus, a sample 10 is irradiated with the laser beam and plasma emission occurs at the sample 10. The emission light passes through the window 9 and is approximately collimated by the collecting lens 8. Then, a part thereof is reflected by the half mirror 7 and enters to a spectroscope 4 after being collected by an incident lens 11. Spectral resolution is performed at the spectroscope 4 and the spectral-resolved light enters to an ICCD camera 5 that is attached to the spectroscope 4. A computer 6 reads out a signal from the ICCD camera 5 to obtain spectral information associated with plasma emission at the sample 10.

In this specification, spectral information obtained by a LIBS analysis device (chemical analysis device) as being associated with plasma emission due to irradiation to a sample with laser light is called a LIBS signal.

Since the emission time of the pulse laser is extremely short, normally, the computer 6 reads out a signal from the ICCD camera 5 with a delay time after a timing signal generator 3 outputs an ON signal of a Q-switch to the pulse laser 1.

CITED DOCUMENT

Non-Patent Document

Non-Patent Document 1: "Development of a portable LIBS-device for quality assurance in concrete repair", A. Taffe et al., Pages 547-549, Concrete Repair, Rehabilitation and Retrofitting ll-Alexander etal. (eds) 2009 Taylor & Francis Group, London, ISBN 978-0-415-46850-3 (http://dicat-a.ing.unibs.it/plizzari/CD/Pdf/075.pdf)

SUMMARY OF THE INVENTION

Such a known LIBS analysis device has problems described below.

[Problem 1]

Since water pressure is high in underwater environment especially at deep sea, the LIBS analysis device is required to be accommodated in a pressure-resistant container. Further, it is required to provide pressure-resistant mechanisms to a cable and a window portion. Such countermeasures are not adopted in a conventional LIBS device.

[Problem 2]

With the conventional LIBS analysis device as illustrated in FIG. 1, it is required that the LIBS analysis device is set to be close to a sample and held at a focal distance of laser light before emitting laser. Here, it is not easy to set the LIBS analysis device as illustrated in FIG. 1 to be faced to a sea bed, a vertical rock at deep sea, or the like. Further, the conventional LIBS analysis device is not suitable to be used for investigation of a sample in a hole at deep sea. Here, it is required to have a mechanism to cause laser light to be faced to a sample held by a submersible or the like. However, the conventional LIBS analysis device is not provided with the mechanism.

[Problem 3]

To obtain a LIBS signal, laser light is required to be focused on a sample at a sea bed or the like. However, the conventional LIBS analysis device as illustrated in FIG. 1 is not provided with a mechanism to perform focusing with a manipulator of a submersible or the like.

[Problem 4]

At a sea bed, laser light is difficult to reach a sample in most cases owing to that deposition substances such as plankton and sludge are accumulated on the sample. In such cases, a satisfactory LIBS signal cannot be obtained. The conventional LIBS analysis device as illustrated in FIG. 1 does not have countermeasures for the above.

[Problem 5]

LIBS signals of metals contained in rocks and deposition substances are mostly in an ultraviolet range, for example, gold being 286 nm, silver being 328 nm, silicon being 199 nm, aluminum being 396 nm, and copper being 324 nm. In contrast, excited laser is near-infrared light, for example, a YAG laser wavelength being 1064 nm, and lenses are used in the conventional LIBS analysis device as illustrated in FIG. 1. Accordingly, color aberration is too large with a lens system, and aberration cannot be sufficiently corrected.

[Problem 6]

The conventional LIBS analysis device as illustrated in FIG. 1 adopts a single pulse laser with a pulse width of laser emission being about 10 nsec. In the case that one laser having the pulse width as described above is used, spectrum inherent to an element under high pressure can be obtained. However, background light (to be stray light) of a LIBS signal is strong and emission intensity of the LIBS signal is low. Further, although relatively stable LIBS signals can be obtained with a liquid sample in water, LIBS signals are weak and unstable having large variation with a solid sample.

An object of the present invention is to provide a device for performing investigation at a sea bed, a lake bed, or a river bed more effectively while solving difficulties of investigation in underwater environment by performing chemical analysis on site especially in underwater environment without taking out a sample.

A chemical analysis device of an aspect of the present invention is a device to analyze a chemical composition of a sample, including a main body that includes a laser light source, a chemical analysis unit, and a housing; an optical head that is arranged to be faced to the sample; and a pressureproof-feedthrough-equipped fiber that is extended from the housing to the optical head to guide laser light emitted from the laser light source to the optical head. The housing houses the laser light source and the chemical analysis unit as having a pressure-resistant function. The optical head includes a mirror system that causes the sample to be irradiated with laser light outgoing from the pressureproof-feedthrough-equipped fiber and to cause plasma emission light occurring at the sample owing to irradiation with the laser light to reenter to the pressureproof-feedthrough-equipped fiber. The chemical analysis unit performs spectroscopic analysis on the plasma emission light that reentered to the pressureproof-feedthrough-equipped fiber.

The pressureproof-feedthrough-equipped fiber may include a single optical fiber and bundle fibers arranged around the single optical fiber. The laser light source may emit long pulse laser light with an emission time being in a range of 200 to 400 nsec. The optical head may include a window through which the laser light passes and LIBS signal light formed of the plasma emission light passes, and the window may include each part of two spherical faces of concentric spheres as an incident face and an outgoing face of light. The optical head may further include a liquid discharging unit to clean a vicinity of the sample. The liquid discharging unit may include a pump that draws liquid at the outside of the optical head, a filter that generates filtrated water by eliminating impurities from the liquid drawn by the pump, and a discharging portion that discharges the filtrated water generated by the filter to the vicinity of the sample. The chemical analysis device may further include a control mechanism that causes the optical head to move for focusing the laser light on the sample. The optical head may include a Cassegrain optical system.

A chemical analysis device according to another aspect of the present invention is a device to analyze a chemical composition of a sample, including a housing that houses a chemical analysis unit as having a pressure-resistant function, an optical head that is arranged to be faced to the sample as having a laser light source for causing plasma emission to occur by irradiating the sample with laser light emitted from the laser light source, a laser control cable that is extended from the housing to the optical head, and an optical fiber that is extended from the optical head to the housing to cause plasma emission light due to plasma emission to enter and to guide the plasma emission light to the chemical analysis unit. The chemical analysis unit performs spectroscopic analysis on the plasma emission light outgoing from the optical fiber.

A chemical analysis device of another aspect of the present invention is a device to analyze a chemical composition of a sample (especially, a sample existing in liquid), including a housing (hereinafter, called a housing main body (especially, being a pressure-resistant container but not necessarily being a pressure-resistant container when not placed in liquid)) that houses a laser light source, a laser controller, and a chemical analysis unit; an optical fiber that is extended especially in liquid from the housing main body to an optical head to cause laser light emitted from the laser light source to enter and to guide the laser light to the optical head that is faced to the sample; the optical head that causes plasma emission to occur by irradiating the sample with the laser light outgoing from the optical fiber and causes the plasma emission light to reenter to the optical fiber; and the chemical analysis unit that performs spectroscopic analysis on the plasma emission light outgoing from the optical fiber.

A chemical analysis device according to another aspect of the present invention is a device to analyze a chemical composition of a sample (especially, a sample existing in liquid), including a housing main body (especially, a pressure-resistant container) that houses a laser light source, a laser controller, and a chemical analysis unit; a first optical fiber that is extended especially in the liquid from the housing main body to an optical head to cause laser light emitted from the laser light source to enter and to guide the laser light to the optical head that is faced to the sample; the optical head that causes plasma emission to occur by irradiating the sample with the laser light outgoing from the first optical fiber; a second optical fiber that is extended especially in the liquid from the optical head to the housing main body to cause plasma emission light due to the plasma emission to enter and to guide the plasma emission light to the chemical analysis unit; and the chemical analysis unit that performs spectroscopic analysis on the plasma emission light outgoing from the second optical fiber.

A chemical analysis device according to another aspect of the present invention is a device to analyze a chemical composition of a sample (especially, a sample existing in liquid), including a housing main body (especially, a pressure-resistant container) that houses a laser controller and a chemical analysis unit, an optical head that is arranged to be faced to the sample as having a laser light source for causing plasma emission to occur by irradiating the sample with laser light emitted from the laser light source, a laser control cable that is extended especially in liquid from the housing main body to the optical head, an optical fiber that is extended in the liquid from the optical head to the housing main body to cause plasma emission light due to plasma emission to enter and to guide the plasma emission light to the chemical analysis unit, and the chemical analysis unit that performs spectroscopic analysis on the plasma emission light outgoing from the optical fiber.

According to the chemical analysis device of the present invention, sample chemical composition can be analyzed on site in environment in liquid while solving abovementioned difficulties of investigation in environment in liquid being underwater or the like, so that investigation at a sea bed, a lake bed, or a river bed (further in sea, in lake, or in river) can be performed more effectively.

EMBODIMENTS OF THE INVENTION

Figure 1:
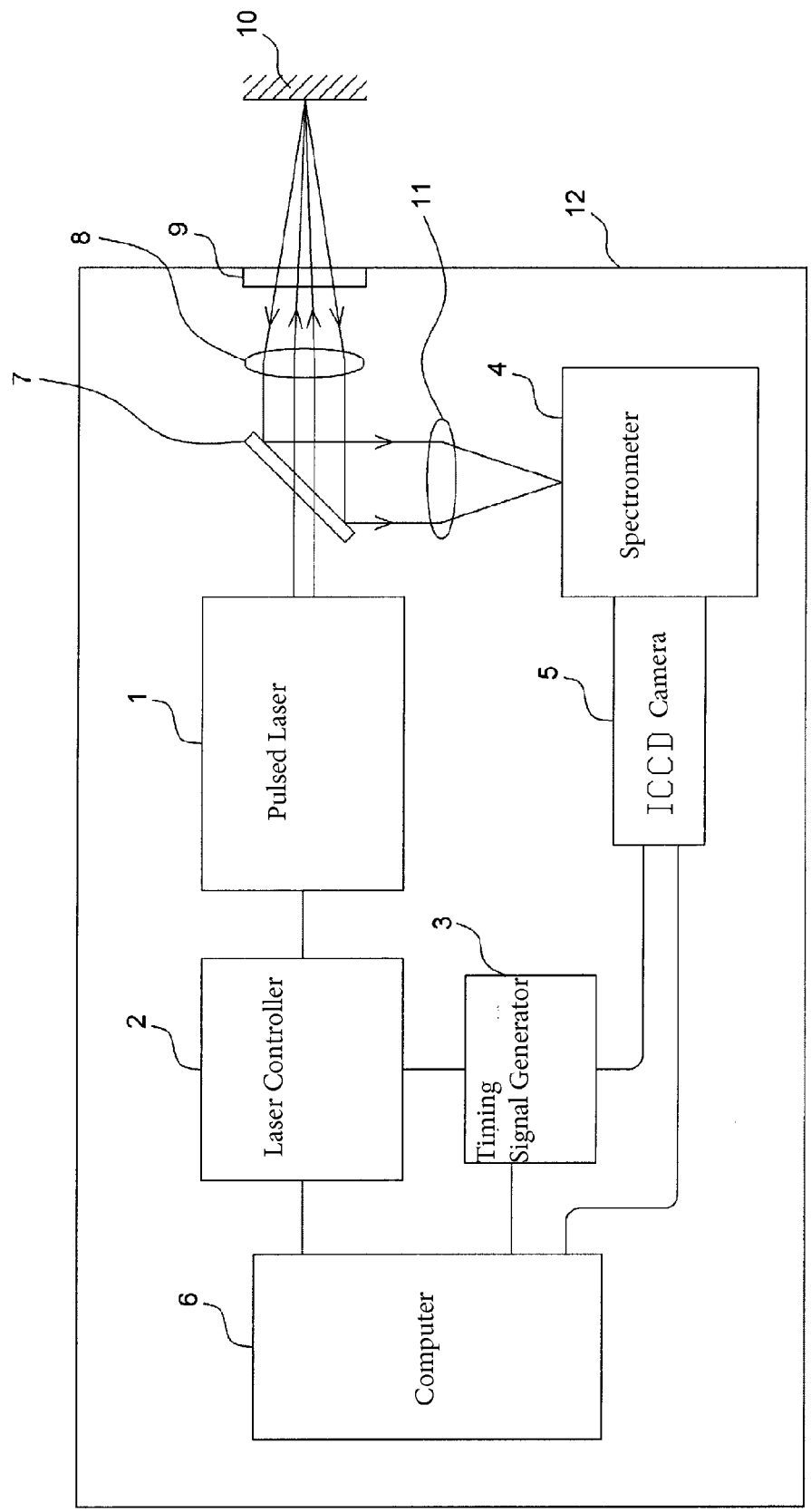
FIG. 1 is a schematic view of a conventional LIBS analysis device.

According to a chemical analysis device of the present invention, problems are solved with all or a part of a plurality of specific countermeasures described below.

[Countermeasure 1]

In consideration of high water pressure, measurement equipment and the like are housed in a pressure-resistant container. Further, in an optical head, a window through which laser light passes has a thickness corresponding to pressure resistance. Here, the window is not flat-plate-shaped but is formed of each part of two concentric spheres. The concentric spheres include shapes similar to the concentric spheres. At each inlet-outlet port of the pressure-resistant container for a cable and an optical fiber, there is provided a mechanism having a pressure-resistant function to be resistant to water pressure and a water-resistant function while causing a fiber to pass therethrough.

[Countermeasure 2]

For allowing to be operated by a manipulator of a submersible, it is required to have a structure to cause laser light to be faced to a sample by a robot and the like. In a chemical analysis device according to an aspect of the present invention, transmitting of laser light and transmitting of LIBS signal light are performed using an optical fiber preferably in a coaxial manner. Accordingly, a light transmitting-receiving portion can be compactified to facilitate a sample at a sea bed or the like to be irradiated with laser light.

[Countermeasure 3]

An optical head is operated by a manipulator of a submersible, so that laser light is caused to be faced to a sample by a robot and the like. Here, the laser light is required to be focused on the sample for irradiation to obtain a satisfactory LIBS signal. Accordingly, a focusing mechanism is required to be arranged. A chemical analysis device according to an aspect of the present invention has a mechanism that can move a laser transmitting portion toward the sample frontward and backward, so that focusing can be performed. Further, a chemical analysis device of an aspect of the present invention has an autofocusing function that focusing can be performed while measuring return light of excited laser light. Thus, laser light can be collected to a sample as being focused thereon.

[Countermeasure 4]

A chemical analysis device according to an aspect of the present invention includes a pump and a filter to discharge clean seawater directly to a sample or to the upper side of the sample, so that environment around the sample is cleaned to prevent laser light and/or a LIBS signal from being interrupted by deposition substances such as plankton and sludge in seawater or at a sea bed. Such cleaning may be performed by discharging water that is stored in a tank.

[Countermeasure 5]

For measuring a LIBS signal, laser light and a LIBS signal are guided not by a lens system but by a mirror system. According to the above, it is possible to prevent signal blur and light expansion to be caused by color aberration. Here, such measurement can be performed even when excited laser wavelength is for near-infrared light and LIBS light is ultraviolet light.

[Countermeasure 6]

Figure 2:
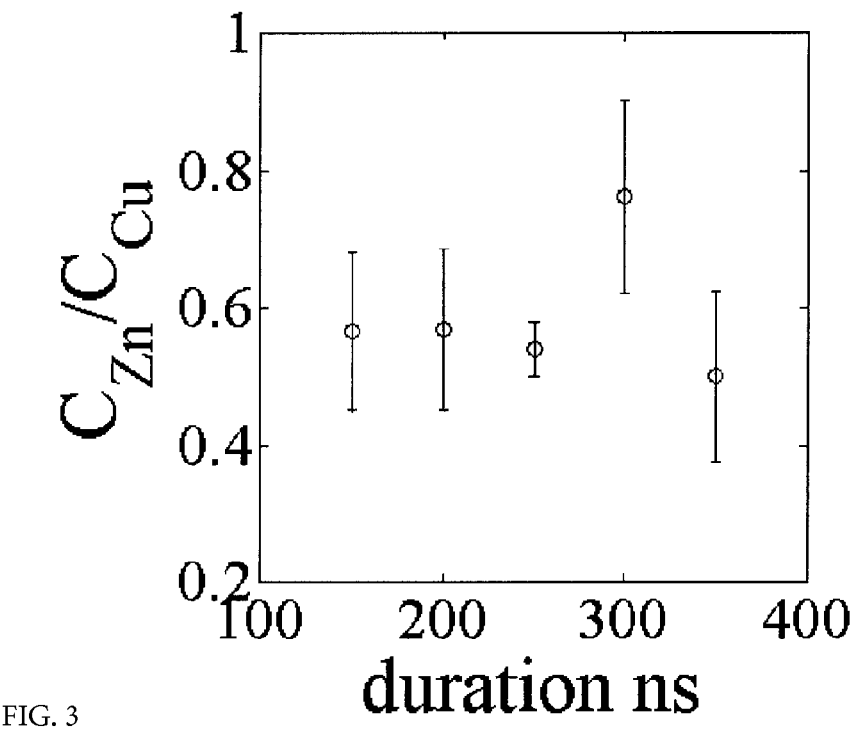
FIG. 2 is a graph indicating errors of measured LIBS signals when mixed material of copper and zinc is irradiated with long pulse laser having a pulse width of 100 to 400 nsec.
Figure 3:
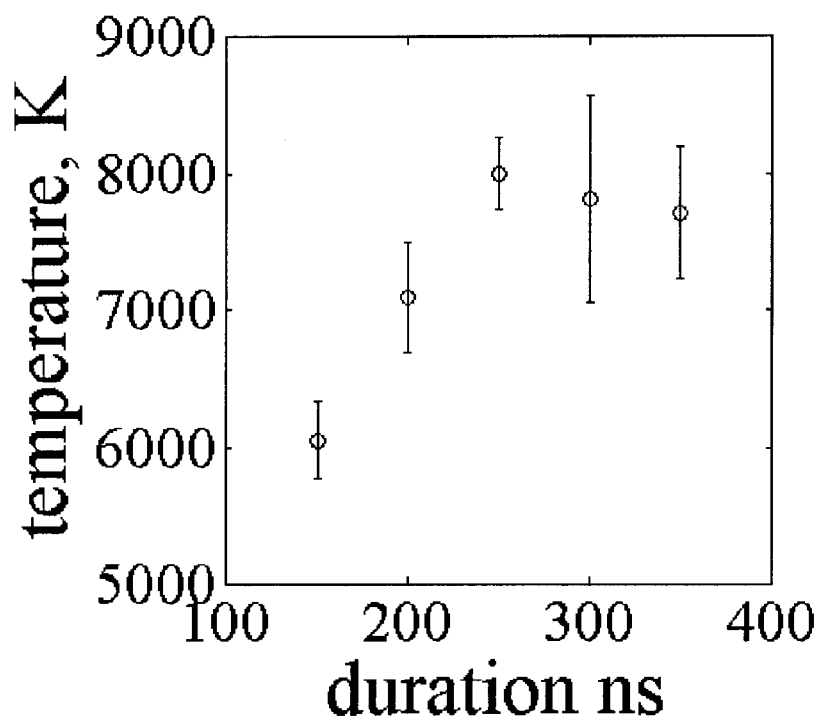
FIG. 3 is a graph indicating measured plasma temperature when a sample is irradiated with long pulse laser having a pulse width of 100 to 400 nsec.
Figure 4:
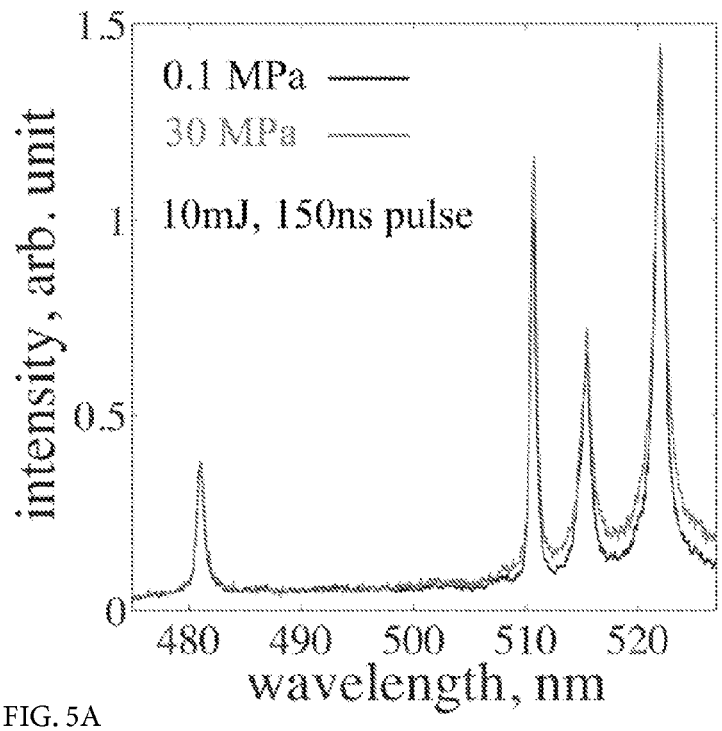
FIG. 4 is a spectrum of LIBS signals obtained through LIBS analysis with long pulse laser.
Figure 5A:
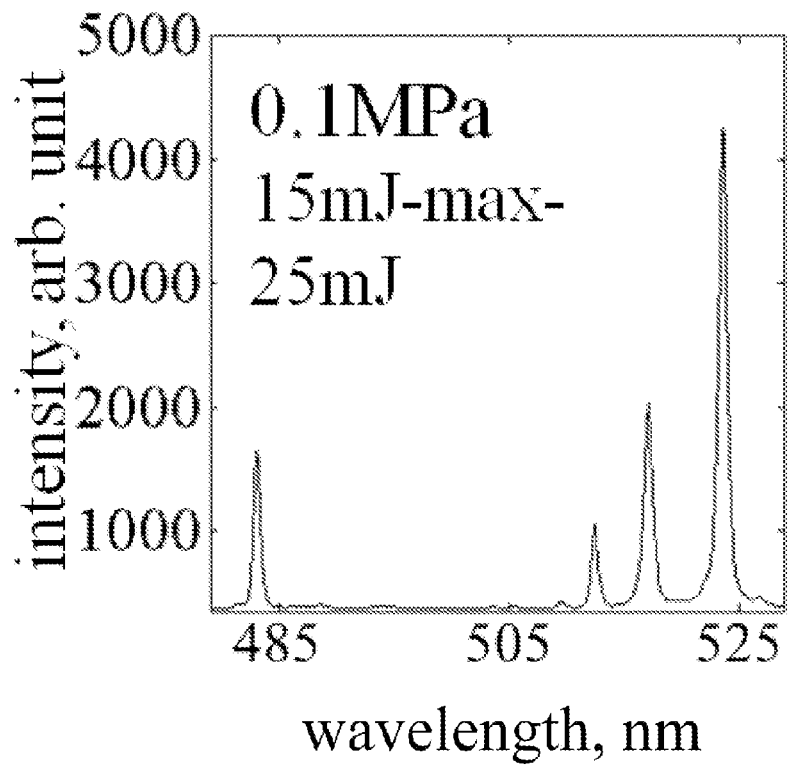
FIG. 5A is a spectrum of LIBS signals obtained through LIBS analysis with double pulse laser.
Figure 5B:
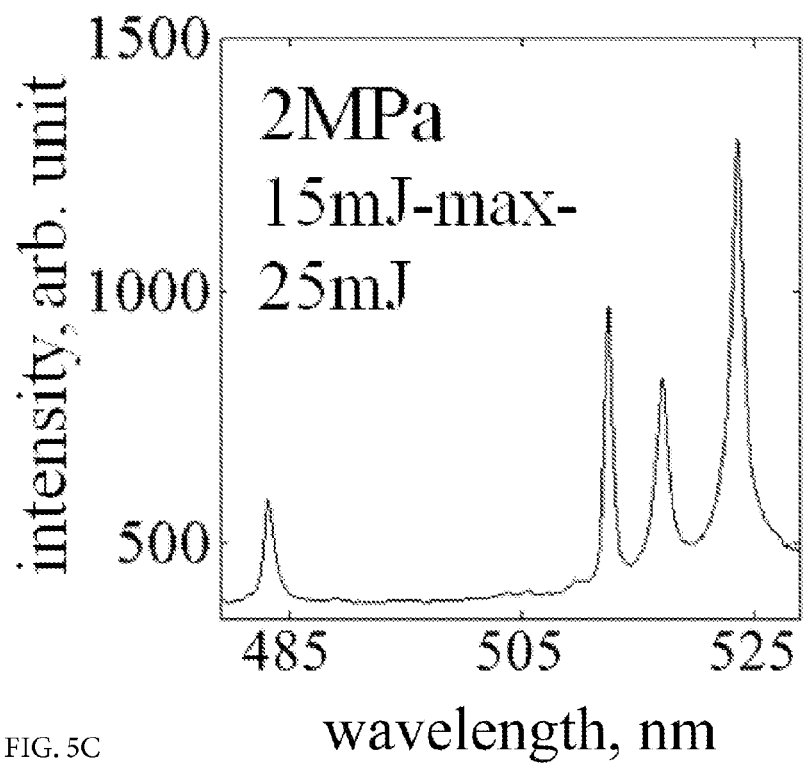
FIG. 5B is a spectrum of LIBS signals obtained through LIBS analysis with double pulse laser.
Figure 5C:
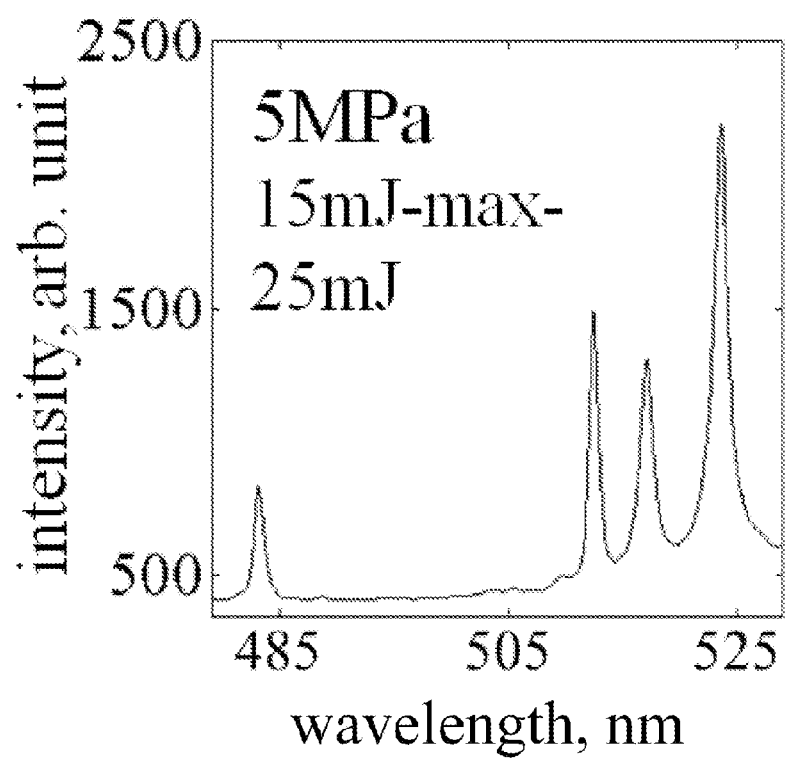
FIG. 5C is a spectrum of LIBS signals obtained through LIBS analysis with double pulse laser.

When a long pulse laser with an emission time being approximately in a range of 200 to 400 nsec (especially about 250 nsec) is used instead of a short single pulse laser with an emission time being approximately 10 nsec, stable LIBS signals having high emission intensity can be obtained from both liquid and solid samples in seawater. In particular, when a long pulse laser with a pulse width being about 250 nsec is used, stable LIBS signals can be obtained with small measurement errors and high plasma temperature, as illustrated in FIGS. 2 and 3. Further, measurement can be performed on liquid and solid samples regardless of the pressure (regardless of being at deep sea or shallow sea), as illustrated in FIG. 4. Further, at shallow sea or in water having a depth of 500 m or less, it is effective to use double pulse lasers using two synchronized single pulse lasers with short laser emission being about 10 nsec. When such double pulse lasers are used, it is possible to obtain stable and clean signals (signals having less background signals to be stray light) as illustrated in FIGS. 5A, 5B, and 5C compared to a case using a single pulse laser for both liquid and solid samples. Here, signals to be obtained are strongly influenced by pressure. FIGS. 4, 5A, 5B, and 5C will be also described later in detail.

(Embodiments)

In the following, embodiments of the present invention will be described in detail.

First, a chemical analysis device of a first embodiment will be described with reference to FIGS. 6A and 6B.

The chemical analysis device of the first embodiment includes a long pulse laser 21 instead of the pulse laser 1 illustrated in FIG. 1 to collect light with an optical fiber and to collect an LIBS signal.

Figure 6A:
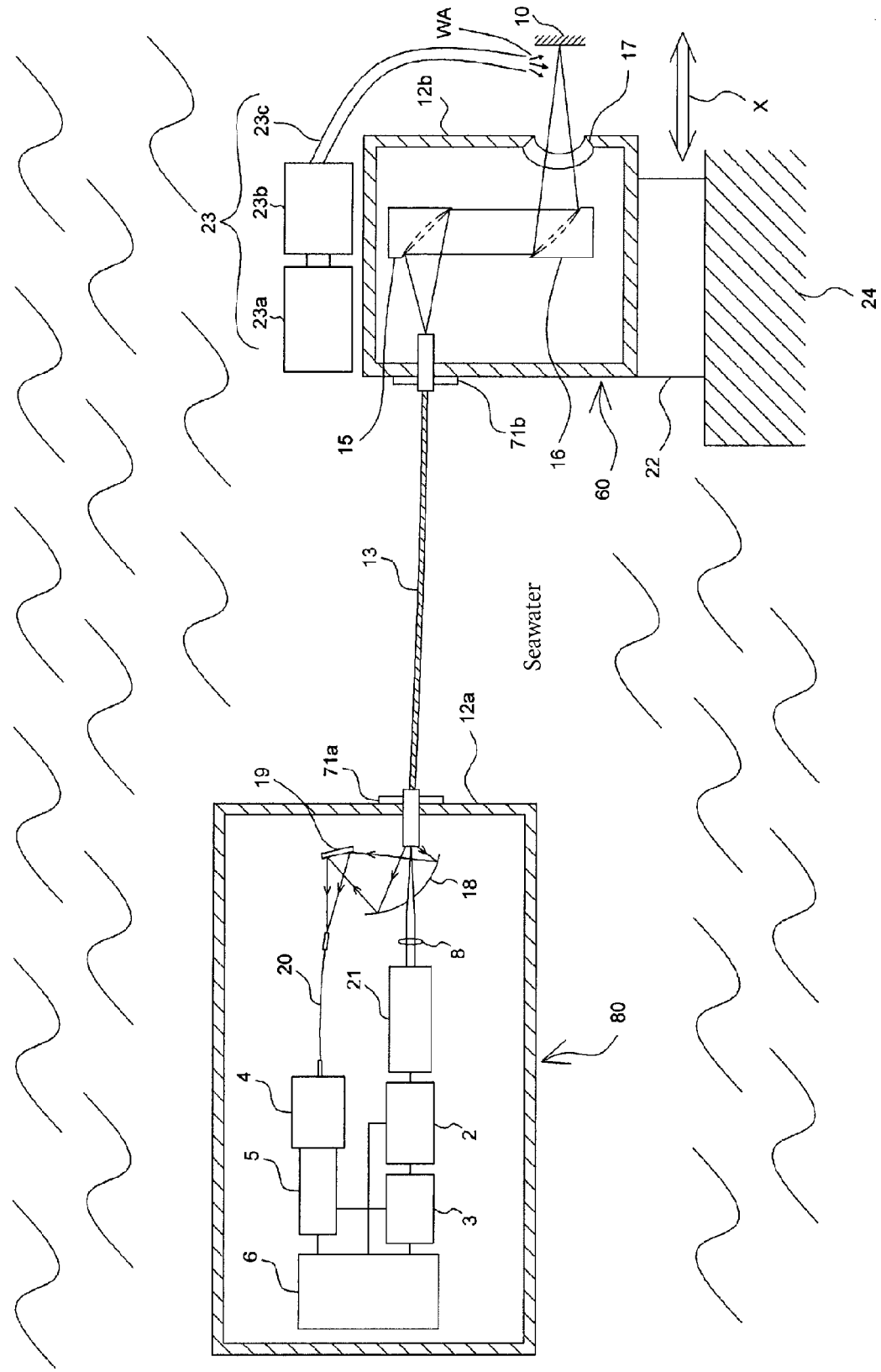
FIG. 6A is a schematic view of a structural example of a LIBS analysis device as a first chemical analysis device.

The chemical analysis device of FIG. 6A includes a main body 80, a first pressureproof-feedthrough-equipped fiber 13, and an optical head 60. The main body 80 includes a pressure-resistant container 12a that is installed in seawater. Laser light emitted from the long pulse laser 21 that is housed in the pressure-resistant container 12a is collected by a collecting lens 8 and is incident on the first pressureproof-feedthrough-equipped fiber 13 after passing through a hole formed at an elliptic mirror 18. In seawater, the laser light is transmitted to the optical head 60 after passing through the first pressureproof-feedthrough-equipped fiber 13.

The optical head 60 includes a pressure-resistant container 12b as a chassis. The laser light outgoing from the first pressureproof-feedthrough-equipped fiber 13 is approximately collimated by a collimation mirror 15. Then, the laser light is collected by a collecting mirror 16 and passes through a spherical window 17 and further through seawater. Thus, a sample 10 is irradiated with the laser light. Here, the laser light is required to be focused on the target sample 10 to obtain a satisfactory LIBS signal. The optical head 60 placed on a robot arm 24 is to be moved in a focusing direction X by a focusing stage 22 and thereby enables the laser light to be focused on the sample 10.

Figure 6B:
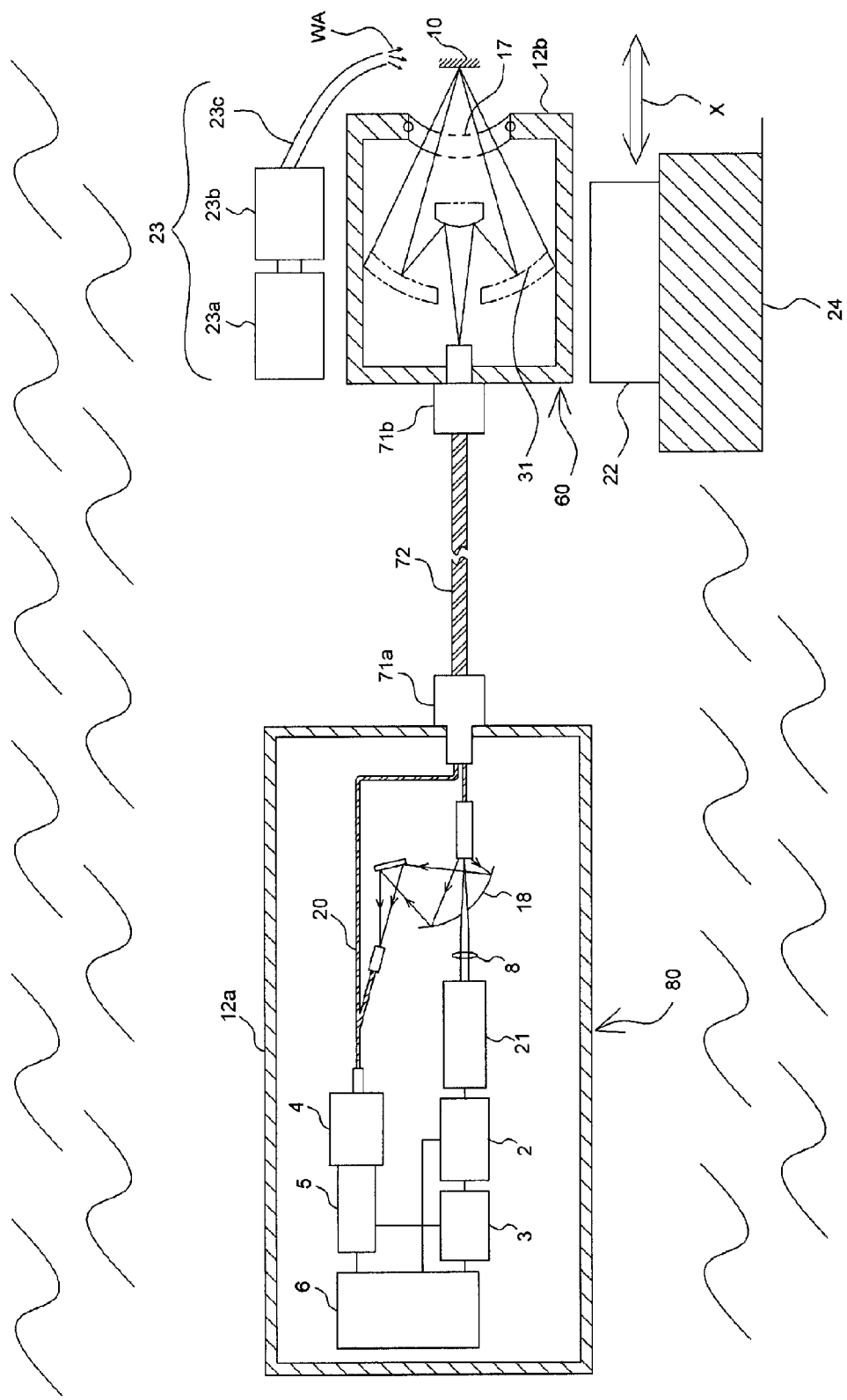
FIG. 6B is a schematic view of a structural example of the LIBS analysis device as the first chemical analysis device.

A difference between FIGS. 6A and 6B is that a chemical analysis device of FIG. 6B includes a second pressureproof-feedthrough-equipped fiber 72 while the chemical analysis device of FIG. 6A includes the first pressureproof-feedthrough-equipped fiber 13. The first pressureproof-feedthrough-equipped fiber 13 will be described later in detail with reference to FIG. 7A. The second pressureproof-feedthrough-equipped fiber 72 will be described later in detail with reference to FIG. 7B. Here, it is also possible that the chemical analysis device of FIG. 6A includes the second pressureproof-feedthrough-equipped fiber 72 instead of the first pressureproof-feedthrough-equipped fiber 13. Further, it is also possible that the chemical analysis device of FIG. 6B includes the first pressureproof-feedthrough-equipped fiber 13 instead of the second pressureproof-feedthrough-equipped fiber 72.

In addition, a difference between FIGS. 6A and 6B is that an optical head 60 of the chemical analysis device of FIG. 6B includes a Cassegrain optical system. Both the first pressureproof-feedthrough-equipped fiber 13 and the second pressureproof-feedthrough-equipped fiber 72 are configured to be resistant to water pressure at deep sea or the like as including a pressure-resistant fiber. Here, the optical head 60 is structured with a mirror system. Accordingly, with either of the chemical analysis devices of FIGS. 6A and 6B, spectrum analysis can be performed in a wide range from ultraviolet to infrared wavelengths without being dependent on wavelengths.

Further, since deposition substances such as plankton and sludge are accumulated on the sample 10 in most cases, a filtrated water supplying portion 23 discharges filtrated water WA or filtrated water WA stored in a tank to a vicinity of the sample 10. Accordingly, the sample 10 can be efficiently irradiated with the laser light and a satisfactory LIBS signal can be obtained. The filtrated water supplying portion 23 includes a pump 23a, a filter 23b, and a discharging portion 23c, for example. Seawater is drawn by the pump 23a, filtrated water WA is generated by eliminating impurities from the drawn seawater with the filter 23b, and the filtrated water WA generated as described above is discharged to a vicinity of the sample 10. As an example, the discharging portion 23c includes a nozzle.

When the sample 10 is irradiated with the laser light, plasma emission occurs at the sample 10. Signal light due to the plasma emission is incident on the first pressureproof-feedthrough-equipped fiber 13 or the second pressureproof-feedthrough-equipped fiber 72 after passing on an opposite route. Light outgoing from the first pressureproof-feedthrough-equipped fiber 13 or the second pressureproof-feedthrough-equipped fiber 72 expands at a fiber-inherent NA value. Then, in the main body 80, the light is reflected by the elliptic mirror 18, and further, reflected by a dichroic mirror 19. Thus, the light is collected to a spectroscope optical fiber 20.

Here, a spherical mirror having a hole formed thereat is adopted instead of the elliptic mirror 18. When the hole-formed spherical mirror is slightly tilted, owing to that aberration thereof is not very large, the light outgoing from the first pressureproof-feedthrough-equipped fiber 13 or the second pressureproof-feedthrough-equipped fiber 72 can be collected to the spectroscope optical fiber 20 without using the elliptic mirror 18.

Figure 7A:
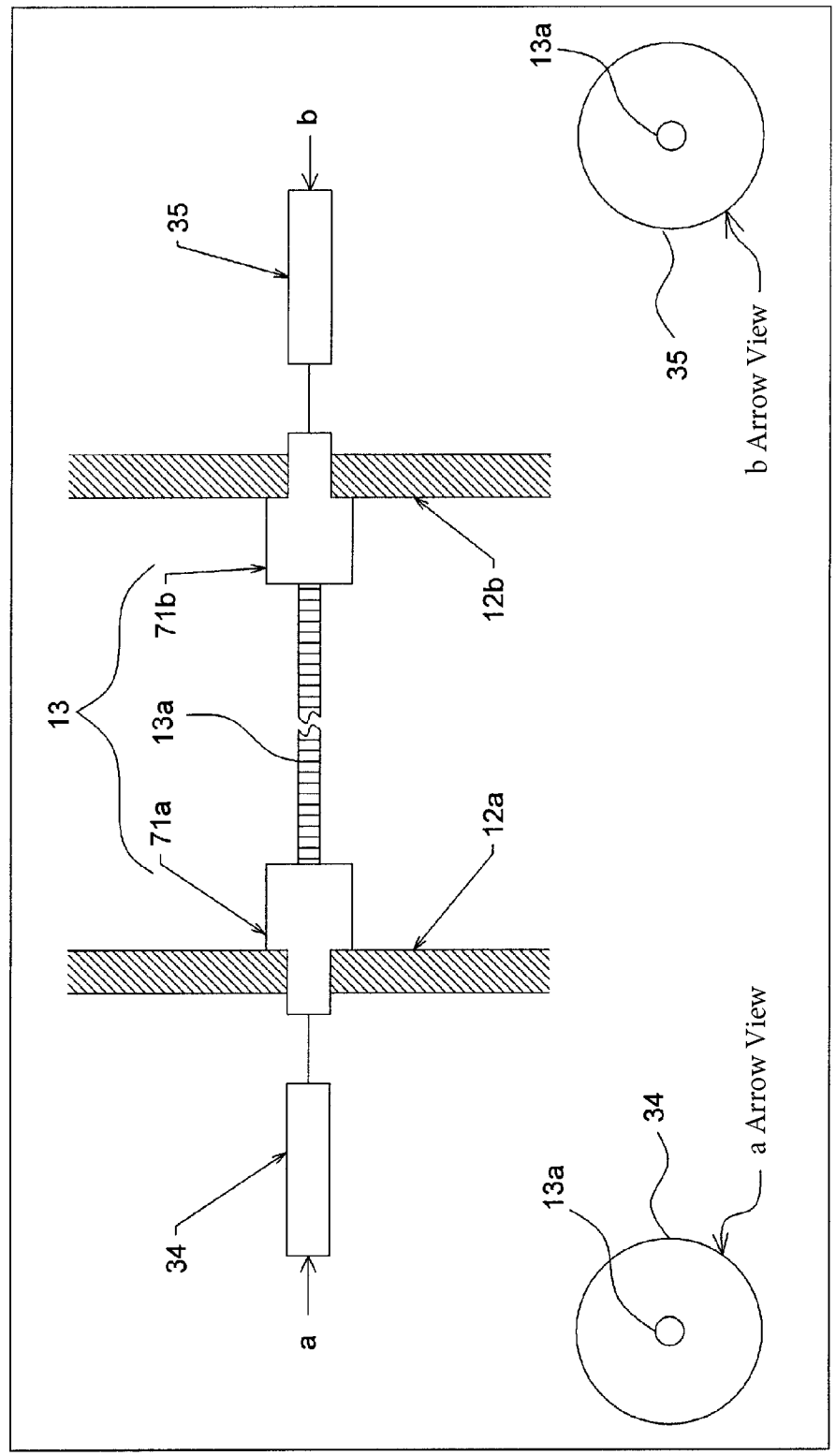
FIG. 7A is an explanatory view of a first pressureproof-feedthrough-equipped fiber.

FIG. 7A is a view for describing the first pressureproof-feedthrough-equipped fiber 13. As illustrated in FIG. 7A, the first pressureproof-feedthrough-equipped fiber 13 includes a fiber pressureproof feedthrough 71a at the main body 80 side, a fiber pressureproof feedthrough 71b at the optical head 60 side, and a pressure-resistant optical fiber 13a. A through-hole is formed at each of the fiber pressureproof feedthrough 71a at the main body 80 side and the fiber pressureproof feedthrough 71b at the optical head 60 side. The fiber pressureproof feedthrough 71a at the main body 80 side and the fiber pressureproof feedthrough 71b at the optical head 60 side are attached to portions of the pressure-resistant containers 12a, 12b respectively where the through-holes are formed. The pressure-resistant optical fiber 13a passes through the respective through-holes.

Both the fiber pressureproof feedthrough 71a at the main body 80 side and the fiber pressureproof feedthrough 71b at the optical head 60 side are configured to be resistant to water pressure at deep sea and attached to the pressure-resistant containers 12a, 12b respectively to prevent seawater at deep sea from entering to the inside of the pressure-resistant containers 12a, 12b. As illustrated in a view on arrow a and a view on arrow b of FIG. 7A, the pressure-resistant optical fiber 13a is a single optical fiber. The pressure-resistant optical fiber 13a located between the fiber pressureproof feedthrough 71a at the main body 80 side and the fiber pressureproof feedthrough 71b at the optical head 60 side is configured to be capable of being resistant to water pressure at deep sea and is covered by sleeves each having a waterproof function to prevent seawater at deep sea from entering to the inside of the pressure-resistant containers 12a, 12b. The pressure-resistant optical fiber 13a is inserted into a spectroscope-side sleeve 34 at the main body 80 side and inserted into an optical-head-side sleeve 35 at the optical head 60 side.

Figure 7B:
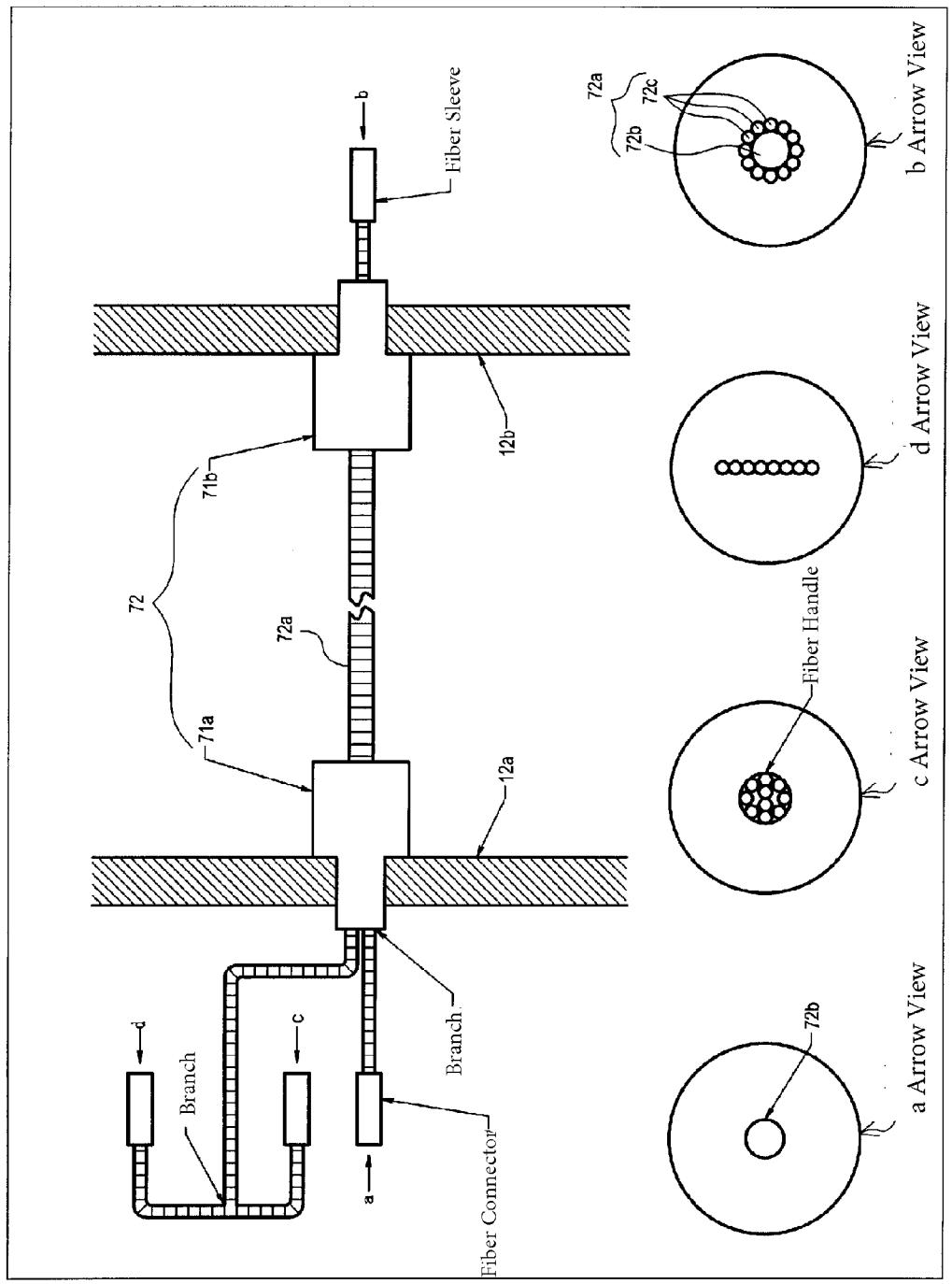
FIG. 7B is an explanatory view of a second pressureproof-feedthrough-equipped fiber.

FIG. 7B is a view for describing the second pressureproof-feedthrough-equipped fiber 72. As illustrated in FIG. 7B, the second pressureproof-feedthrough-equipped fiber 72 includes a fiber pressureproof feedthrough 71a at the main body side, a fiber pressureproof feedthrough 71b at the optical head 60 side, and a pressure-resistant optical fiber 72a. A difference between the second pressureproof-feedthrough-equipped fiber 72 of FIG. 7B and the first pressureproof-feedthrough-equipped fiber 13 of FIG. 7B is that the second pressureproof-feedthrough-equipped fiber 72 includes the pressure-resistant optical fiber 72a while the first pressureproof-feedthrough-equipped fiber 13 includes the pressure-resistant optical fiber 13a.

As illustrated in a view on arrow b of FIG. 7B, the pressure-resistant optical fiber 72a includes a single optical fiber 72b and bundle fibers 72c placed around the single optical fiber 72b. The single optical fiber 72b is a fiber through which laser light passes and plasma light from the sample 10 passes. The bundle fibers 72c are fibers through which light that does not pass through the single optical fiber 72b among the plasma light from the sample 10 passes. That is, even in a case that the plasma light (LIBS signal light) from the sample 10 is expanded, the pressure-resistant optical fiber 72a can transmit, by the bundle fibers 72c to the spectroscope 4 in the main body 80, light that cannot be transmitted through the single optical fiber 72b among the LIBS signal light.

The pressure-resistant optical fiber 72a located between the fiber pressureproof feedthrough 71a at the main body 80 side and the fiber pressureproof feedthrough 71b at the optical head 60 side is configured to be capable of being resistant to water pressure at deep sea and is covered by sleeves each having a waterproof function to prevent seawater at deep sea from entering to the inside of the pressure-resistant containers 12a, 12b.

Since the long pulse laser 21 is used in the abovementioned embodiment, a strong and stable LIBS signal can be obtained for both of a liquid sample and a solid sample without being dependent on water depth. Here, the long pulse laser 21 emits long pulse laser light having a transmission time being in a range of 200 to 400 nsec.

Further, since the first pressureproof-feedthrough-equipped fiber 13 or the second pressureproof-feedthrough-equipped fiber 72 is used, a sea bed or a sample at a side face of a hole at a vicinity of the sea bed can be easily irradiated with laser light.

Further, since mirrors are used in a light emitting system and a light receiving system, ultraviolet light can be measured as well without having color aberration due to wavelengths.

Further, since the focusing stage 22 is used, focusing of laser light can be easily performed even with a manipulator of a submersible. Further, since the filtrated water supplying portion 23 is used, a satisfactory LIBS signal can be obtained even in muddy water.

Further, since the spherical window 17 is used, reflection light of the emitted laser light is not collected in the window to prevent the window from being damaged. Furthermore, since the spherical window 17 has a spherical shape, there is an advantage that an aberration problem is not caused at the time of light collecting and light receiving owing to that collected light is not refracted.

Figure 8A:
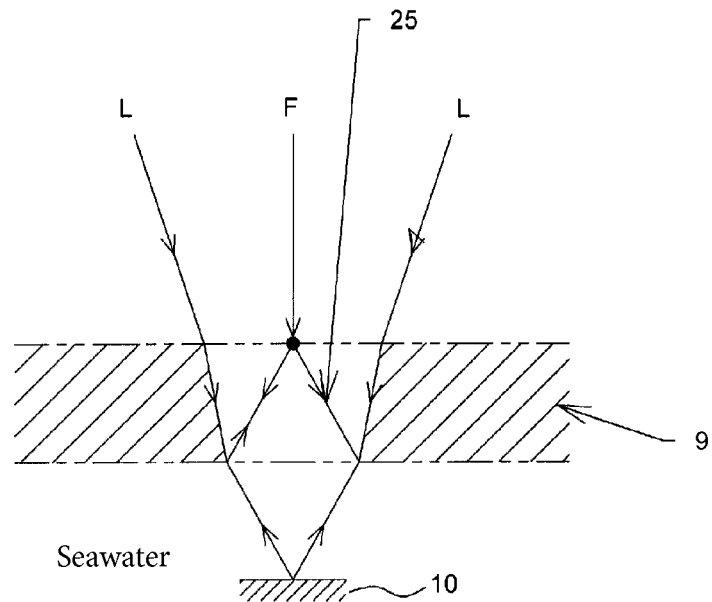
FIG. 8A is a schematic view of a window of a conventional optical head.
Figure 8B:
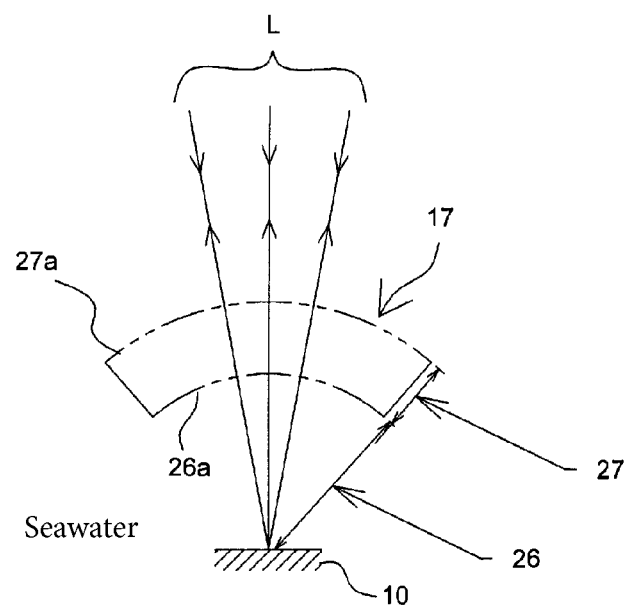
FIG. 8B is a schematic view of a spherical window of an optical head of an embodiment.

FIG. 8A illustrates a conventional flat-plate-shaped window 9 and FIG. 8B illustrates the spherical window 17 of the present embodiment. Here, comparison between the conventional flat-plate-shaped window 9 and the spherical window 17 of the present embodiment is performed with reference to FIGS. 8A and 8B. Laser light L is refracted at the conventional flat-plate-shaped window 9 illustrated in FIG. 8A. Accordingly, aberration occurs to cause a problem such as defocusing. In addition, since the plate 9 is flat-plate-shaped, there is a possibility that the window 9 is damaged with heat owing to that reflection light 25 occurs from a surface of the window 9 and is collected to a focal point F. As illustrated in FIG. 8B, the spherical window 17 of the present embodiment has a first face 26a having a first radius 26 equivalent to a length r1 and a second face 27a having a second radius 27 equivalent to a length r2 that is longer than the length r1. The first face 26a and the second face 27a form a part of concentric spheres. Alternatively, not necessarily being concentric, the first face 26a and the second face 27a are structured with faces that are close to concentric spheres. The second face 27a is formed to have a curvature radius so that light returning therefrom is not focused at a mirror or in a lens system located at a near side. Accordingly, the mirror and the lens system are prevented from being damaged by the returning light from the second face 27a and collected laser light is prevented from being largely refracted. The spherical window 17 is placed so that laser light passed through the spherical window 17 is collected at one point of the sample 10. In this case, aberration does not occur at the collected light or aberration is small even when it occurs, so that near-infrared laser excitation light and a LIBS signal of plasma light having an ultraviolet wavelength pass coaxially through the same light path.

Figure 9:
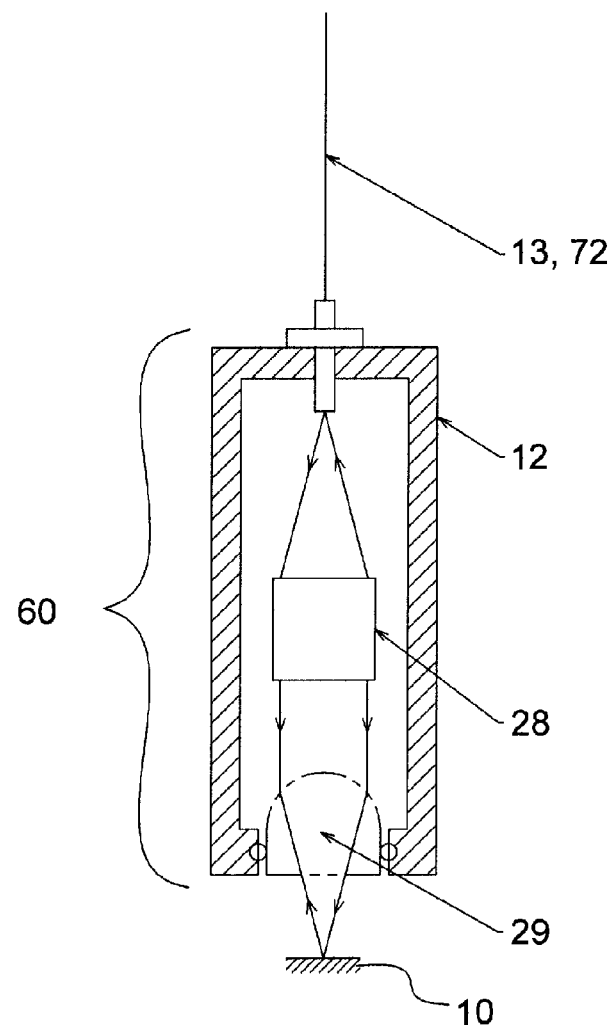
FIG. 9 is a sectional view of a structural example of an optical head.

Description will be provided on an example that the optical head is structured with a lens system with reference to FIG. 9.

The first pressureproof-feedthrough-equipped fiber 13 or the second pressureproof-feedthrough-equipped fiber 72 is arranged as being extended from the pressure-resistant container 12a that houses the long pulse laser 21, the spectroscope 4, an ICCD camera 5, a computer 6, and the like that are illustrated in FIGS. 6A and 6B. In FIGS. 6A and 6B, the optical head 60 is structured with a mirror system. In an example of FIG. 9, the optical head 60 is structured with a lens system.

When aberration correction is to be easily performed while a wavelength band of a LIBS signal is not for ultraviolet light, there may be a case that an optical system in the optical head can be structured with a lens system. With a lens system, there occurs color aberration depending on a wavelength. However, when such color aberration can be lessened, a lens system can be adopted. Compared to mirrors, lenses have advantages of easier availability and capability of providing more compact system.

Laser light outgoing from the first pressureproof-feedthrough-equipped fiber 13 or the second pressureproof-feedthrough-equipped fiber 72 is collected to the sample 10 through a lens system 28 and a pressure-resistant window and lens 29. LIBS signal light is incident on the first pressureproof-feedthrough-equipped fiber 13 or the second pressureproof-feedthrough-equipped fiber 72 after passing on an opposite route. At that time, the LIBS signal light may not enter to the first pressureproof-feedthrough-equipped fiber 13 entirely owing to color aberration depending on wavelength. Here, in a case that the LIBS signal light is strong and a case that light is collected around a core of the first pressureproof-feedthrough-equipped fiber 13 with small aberration, it is also possible to use the optical head 60 of FIG. 9.

In the optical head 60 of FIG. 9, the pressure-resistant window and lens 29 serves as a pressure-resistant window and a collecting lens.

Figure 10A:
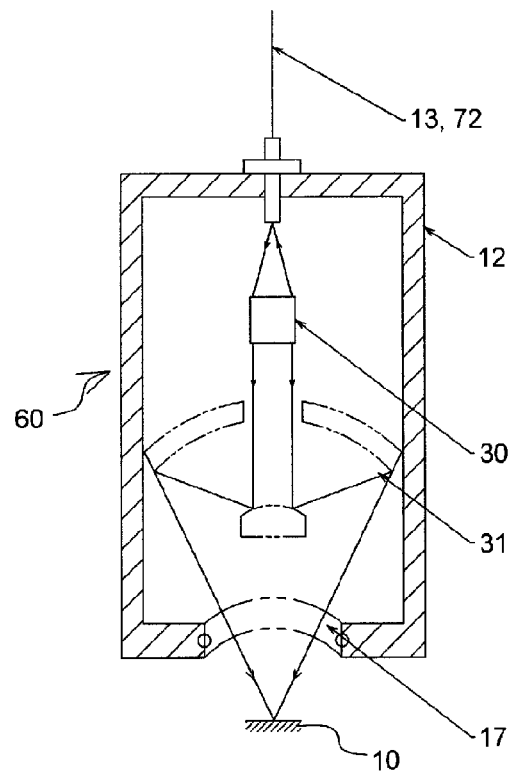
FIG. 10A is a sectional view of another structural example of the optical head.
Figure 10B:
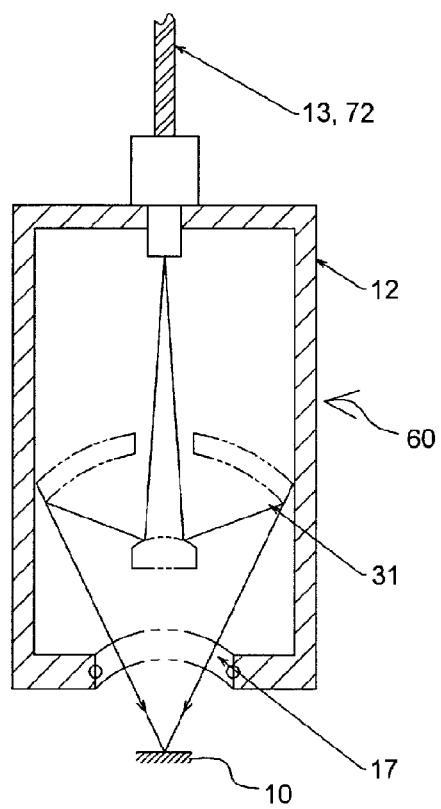
FIG. 10B is a sectional view of another structural example of the optical head.

FIGS. 10A and 10B illustrate examples in which the optical head 60 is structured with a Cassegrain optical system.

Similarly to the optical head 60 of FIG. 9, in the optical head 60 of FIGS. 10A and 10B, the first pressureproof-feedthrough-equipped fiber 13 or the second pressureproof-feedthrough-equipped fiber 72 is arranged as being extended from the pressure-resistant container 12a that houses the long pulse laser 21, the spectroscope 4, the ICCD camera 5, the computer 6, and the like that are illustrated in FIGS. 6A and 6B. Following is description on an example that the optical head 60 is structured with a Cassegrain optical system. With the optical head 60 of FIG. 10A, laser light outgoing from the first pressureproof-feedthrough-equipped fiber 13 or the second pressureproof-feedthrough-equipped fiber 72 is approximately collimated by a collimation lens 30, enters to the Cassegrain optical system 31, and passes through the spherical window 17. Thus, the sample 10 is irradiated with the laser light. LIBS light returns to the first pressureproof-feedthrough-equipped fiber 13 or the second pressureproof-feedthrough-equipped fiber 72 on the opposite optical path. With the optical head 60 of FIG. 10B, laser light outgoing from the first pressureproof-feedthrough-equipped fiber 13 or the second pressureproof-feedthrough-equipped fiber 72 directly enters to the Cassegrain optical system 31 and passes through the spherical window 17. Thus, the sample 10 is irradiated with the laser light. LIBS light returns to the first pressureproof-feedthrough-equipped fiber 13 or the second pressureproof-feedthrough-equipped fiber 72 on the opposite optical path.

Figure 11:
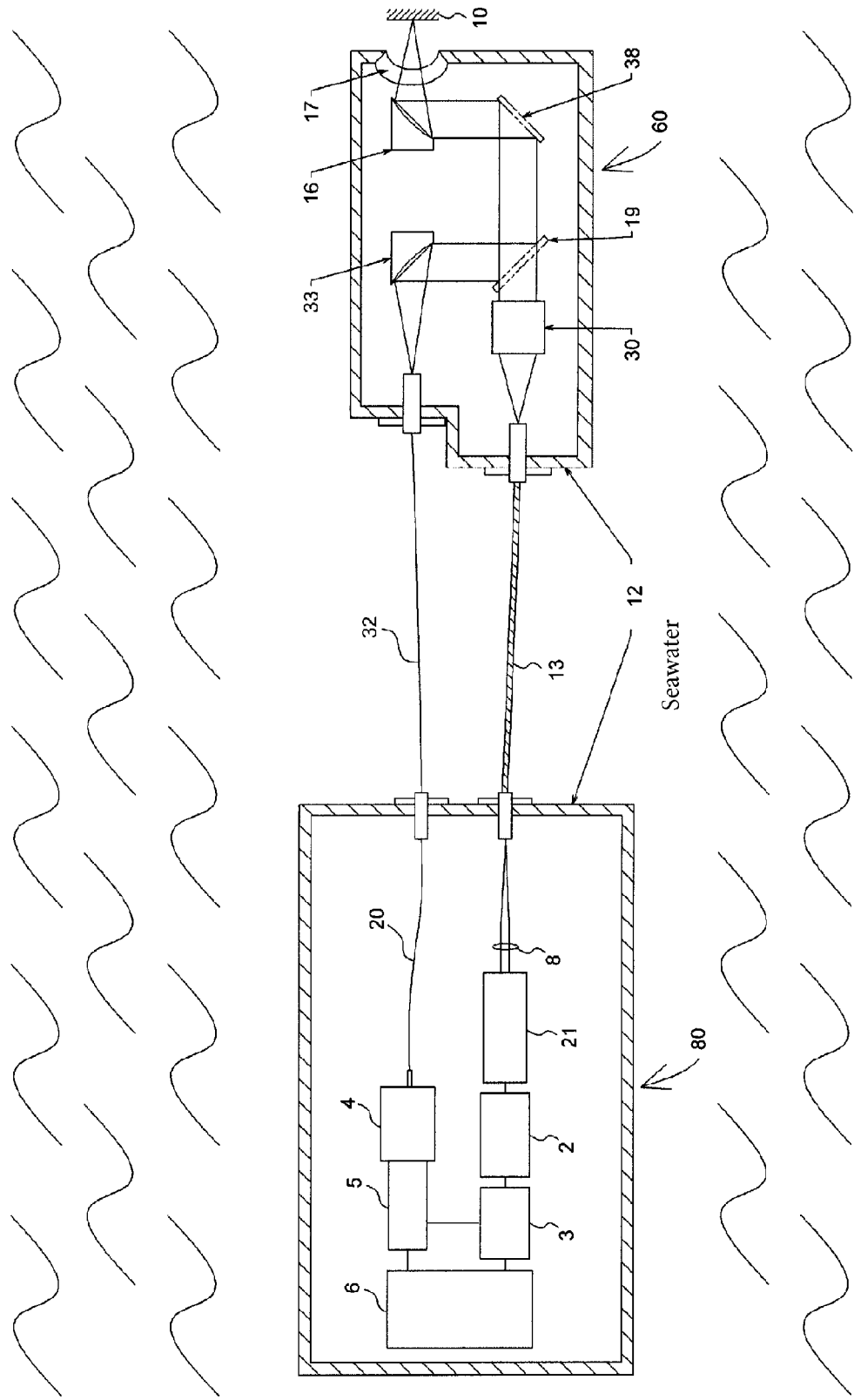
FIG. 11 is a schematic view of a structural example of a LIBS analysis device as a second chemical analysis device.

FIG. 11 is a view illustrating a chemical analysis device according to a second embodiment.

Laser light passes through the first pressureproof-feedthrough-equipped fiber 13 and is collimated by the collimation lens 30 in the optical head 60. Then, after being reflected by a reflection mirror 38, the laser light is collected by the collecting mirror 16 and passes through the spherical window 17. Thus, the sample 10 is irradiated with the laser light. LIBS signal light passes on the opposite optical path. Light only in a wavelength band of the LIBS signal light is reflected by the dichroic mirror 19 and is incident on a pressureproof-feedthrough-equipped fiber bundle 32 with a collecting mirror 33. The pressureproof-feedthrough-equipped fiber bundle 32 is guided to a slit of the spectroscope 4 in the main body 80.

Figure 12:
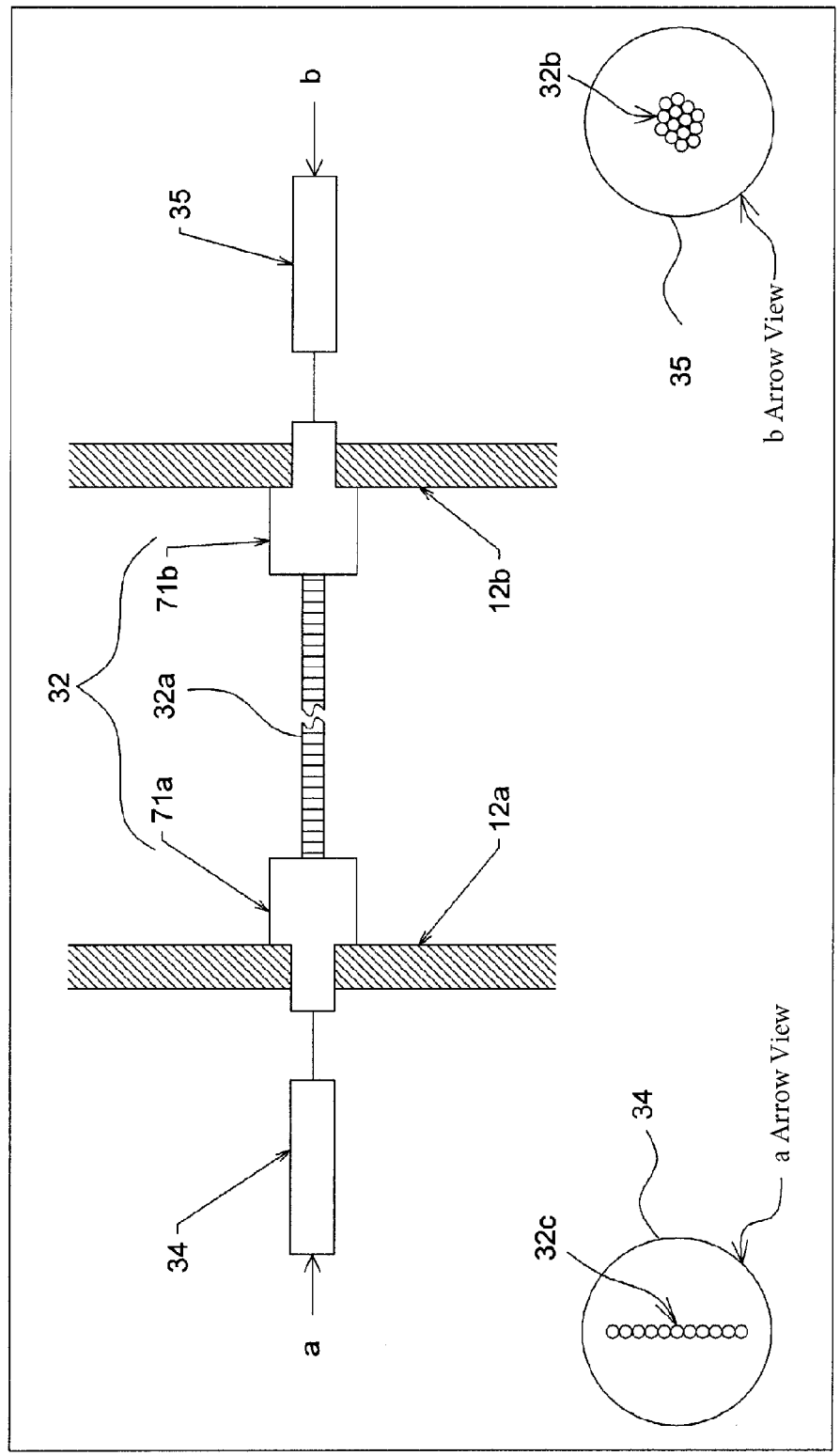
FIG. 12 is a structural view of a pressureproof-feedthrough-equipped fiber bundle.

The pressureproof-feedthrough-equipped fiber bundle 32 is structured as illustrated in FIG. 12.

The pressureproof-feedthrough-equipped fiber bundle 32 is structured by binding several optical fiber elements. The optical-head-side sleeve 35 is configured so that the plurality of optical fiber elements 32b are arranged at the vicinity of the center as illustrated in a view on arrow b to facilitate the LIBS signal light collected by the collecting mirror 33 of FIG. 11 to enter to the pressureproof-feedthrough-equipped fiber bundle 32. Meanwhile, as illustrated in a view on arrow a, the plurality of optical fiber elements 32c are aligned at the spectroscope-side sleeve 34. This is because the slit of the spectroscope 4 is opened in an elongated manner.

Figure 13A:
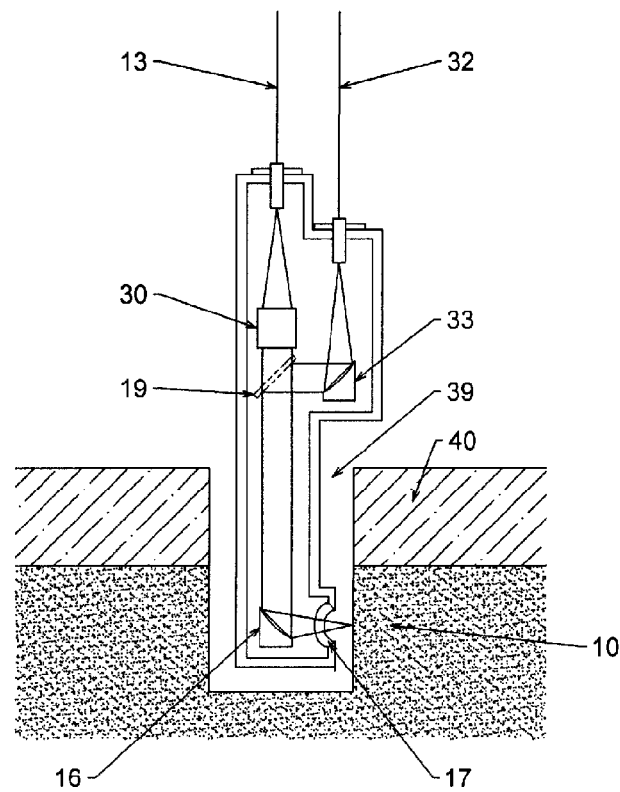
FIG. 13A is a sectional view of a structural example of an optical head capable of being used in the LIBS analysis device.

FIG. 13A illustrates an example of an elongated optical head using a mirror system.

Figure 13B:
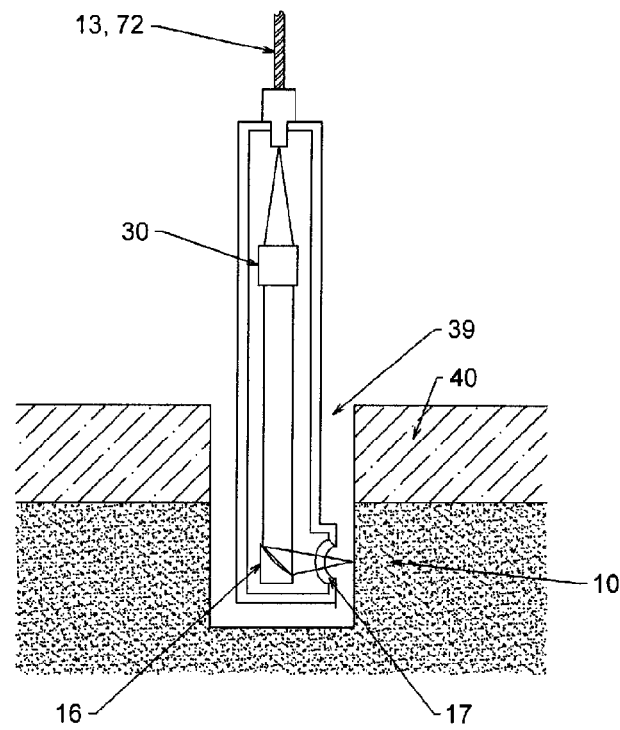
FIG. 13B is a sectional view of a structural example of the optical head capable of being used in the LIBS analysis device.

Similarly to FIG. 11, the first pressureproof-feedthrough-equipped fiber 13 is connected to a portion on which laser light is incident and the pressureproof-feedthrough-equipped fiber bundle 32 is connected to the spectroscope 4. Laser light outgoing from the first pressureproof-feedthrough-equipped fiber 13 is collimated by the collimation lens 30 and passes through the inside of an elongated pressure-resistant container. Then, the laser light passes through the spherical window 17 as being collected by the collecting mirror 16 and is focused on the sample 10. The reason why the optical head is elongated as described above is to facilitate to obtain a LIBS signal of the sample 10 such as a targeted rock after forming a borehole 39 at the sea bed or the like and eliminating deposition substances 40 and the like. With the optical head of FIG. 13A, a sample at a side face of a borehole can be measured. FIG. 13B illustrates an example of an elongated optical head using a mirror system and a collimation lens. The optical head of FIG. 13B adopts the first pressureproof-feedthrough-equipped fiber 13 or the second pressureproof-feedthrough-equipped fiber 72.

Figure 14:
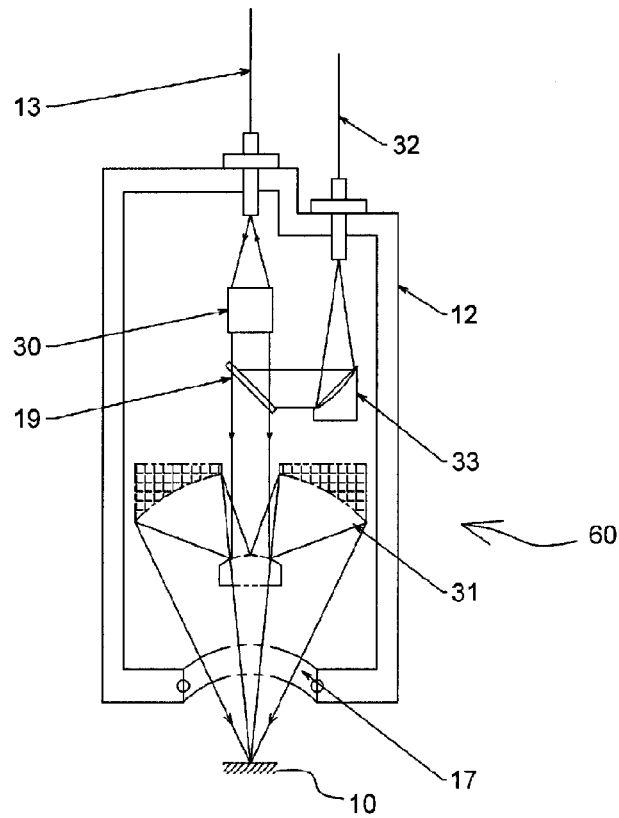
FIG. 14 is a sectional view of a structural example of another optical head.

FIG. 14 illustrates an example in which an optical head is structured with a Cassegrain optical system.

Similarly to an example in which the optical head is structured with the Cassegrain optical system as illustrated in FIGS. 10A and 10B, the optical head of FIG. 14 is structured with the Cassegrain optical system. Here, the dichroic mirror 19 is arranged at some midpoint, so that reflected LIBS signal light is transmitted after being collected to the pressureproof-feedthrough-equipped fiber bundle 32 by the collecting mirror 33.

In general, laser light is near-infrared light as a fundamental wave of YAG laser (1064 nm). When a wavelength band of the LIBS signal light corresponds to ultraviolet light, the first pressureproof-feedthrough-equipped fiber 13 also has a function of transmitting the LIBS signal light in a case of FIGS. 10A and 10B. In this case, color aberration cannot be eliminated only by the collimation lens 30, so that the LIBS signal light does not enter to the first pressureproof-feedthrough-equipped fiber 13. In contrast, when the LIBS signal light is separated by the dichroic mirror 19 as illustrated in FIG. 14, influence of color aberration is eliminated owing to that the LIBS signal passes only through the mirror system. Obviously, since the spherical window 17 is used for collecting light, color aberration does not influence thereto.

Figure 15:
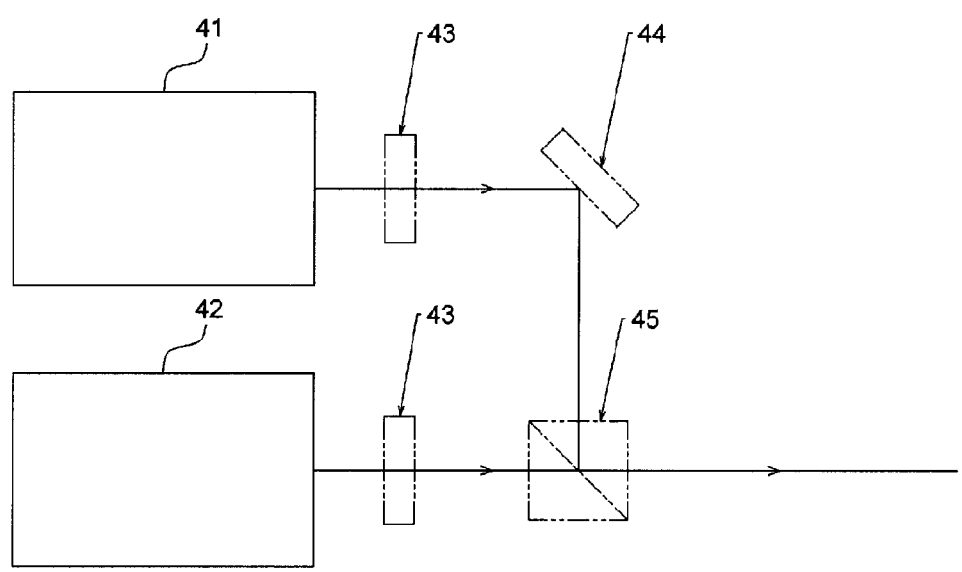
FIG. 15 is a structural view of a laser light source.

FIG. 15 illustrates an example using double pulse lasers. Here, the pulse lasers being a first pulse laser 41 and a second pulse laser 42 are adopted. Light outgoing from the respective lasers is adjusted by half-wavelength plates 43 to have polarization being mutually orthogonal. Laser light outgoing from the first pulse laser 41 is reflected by a reflection mirror 44 and synthesized at a polarization beam splitter 45. The polarization beam splitter 45 has a function to reflect laser light from the first pulse laser 41 and to transmit laser light from the second pulse laser 42 having polarization orthogonal thereto. Accordingly, optical axes of the double laser light can be matched to each other with little energy damping. The double pulse lasers may be replaced with the single pulse laser and the long pulse laser described above.

In the case of adopting the double pulse lasers, the first pulse laser 41 emits laser light, and after an appropriate delay time, the second pulse laser 42 emits laser light as well. With the above, at shallow sea such as a continental shelf having a depth of 500 m or less, a river bed, and a lake bed, more stable and more satisfactory LIBS signal light can be obtained for both of a liquid sample and a solid sample than that obtained only with a single laser.

Figure 16:
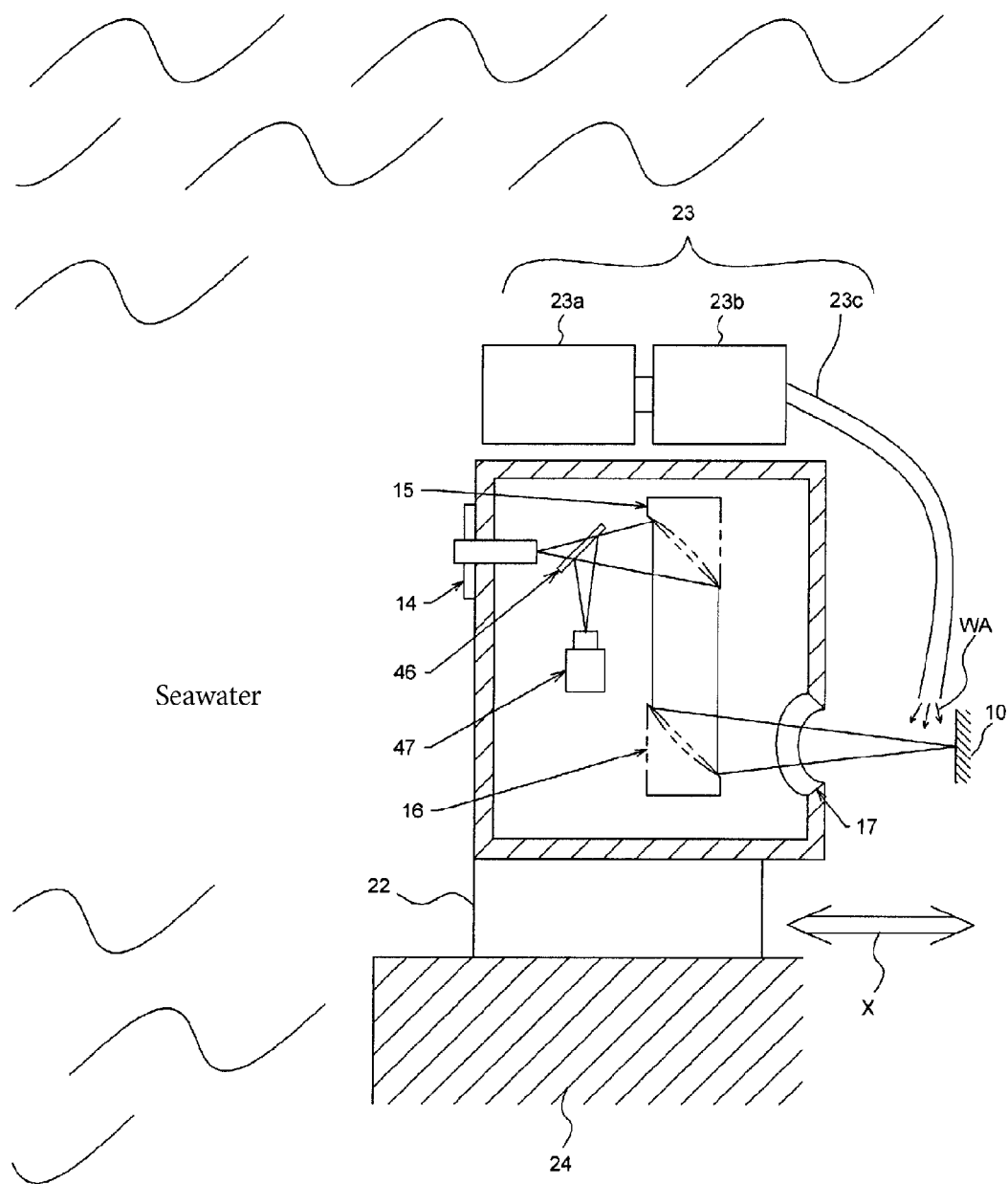
FIG. 16 is a sectional view of a structural example of another optical head.

FIG. 16 illustrates an example using a camera for focusing. In the example of FIG. 16, a partial-reflection mirror 46 is arranged in the optical head 60, so that a part of laser light collected to the sample 10 returns and enters to a camera 47 as being reflected by the partial-reflection mirror 46. When being performed along with the focusing stage 22, detection with the camera 47 can be utilized for autofocusing of laser light. Here, when the laser light is focused on the sample 10, an image of the laser light becomes to a spot on the sample and luminance thereof becomes high. Accordingly, owing to that the detection with the camera 47 is performed along with the focusing stage 22, focusing can be performed. Such a configuration can be also utilized as being arranged at another optical head.

Figure 17:
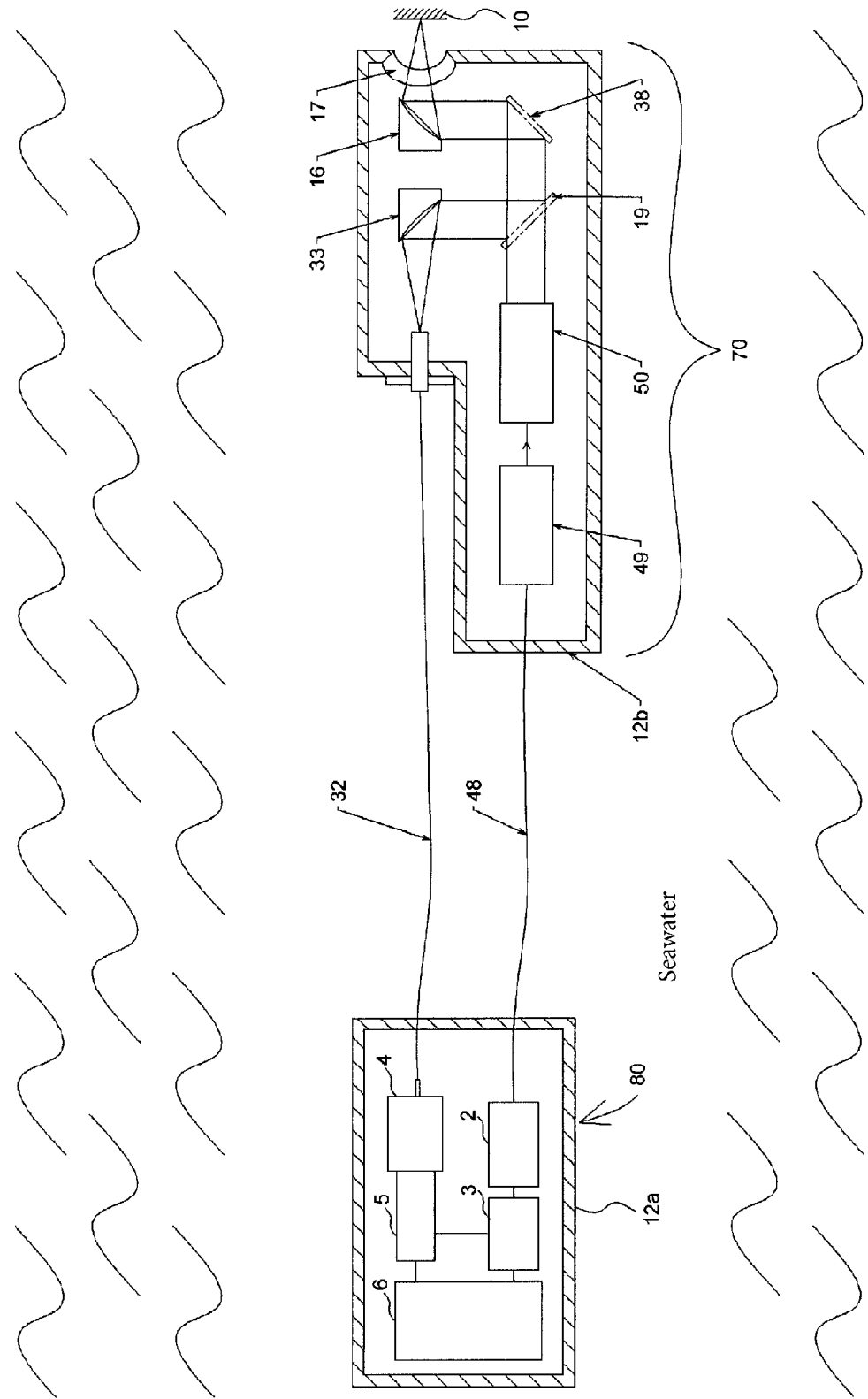
FIG. 17 is a schematic view of a structural example of a LIBS analysis device as a third chemical analysis device.

Next, a chemical analysis device according to a third embodiment is described with reference to FIG. 17. In the chemical analysis device according to the third embodiment, a laser is mounted on an optical head.

A small laser 49 is mounted on an optical head 70. The small laser 49 is controlled via a laser control cable 48 that extends from the pressure-resistant container 12a. Laser light emitted from the small laser 49 has a beam diameter that is to be expanded by a laser beam expander 50 and is reflected by the reflection mirror 38. Then, the laser light passes through the spherical window 17 as being collected by the collecting mirror 16. Thus, the sample 10 is irradiated with the laser light.

LIBS signal light passes on the opposite optical path after being reflected by the dichroic mirror 19, is collected by the collecting mirror 33, enters to the pressureproof-feedthrough-equipped fiber bundle 32, and is transmitted to the spectroscope 4 in the main body 80. Here, when the optical head 70 is structured compact with the compactified laser, there arise advantages that the beam diameter of a collection point on the sample 10 can be lessened compared to a case of using a fiber, and the like.

Some of the examples described above may not include the filtrated water supplying portion 23, the focusing mechanism such as the focusing stage 22, and the like. However, it is also possible to include the above if needed. Further, the long pulse laser 21 may be used as being replaced with a single pulse laser or a double pulse laser.

Following are results of LIBS analysis in liquid with the abovementioned examples.

Figure 18A:
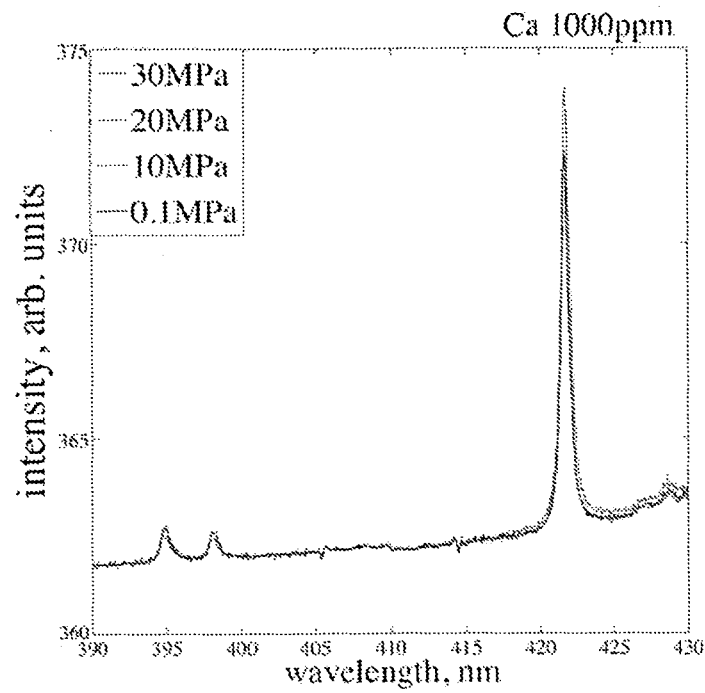
FIG. 18A is a view illustrating LIBS signals of dissolved calcium in liquid at 0.1 MPa, 10 MPa, 20 MPa, and 30 MPa.
Figure 18B:
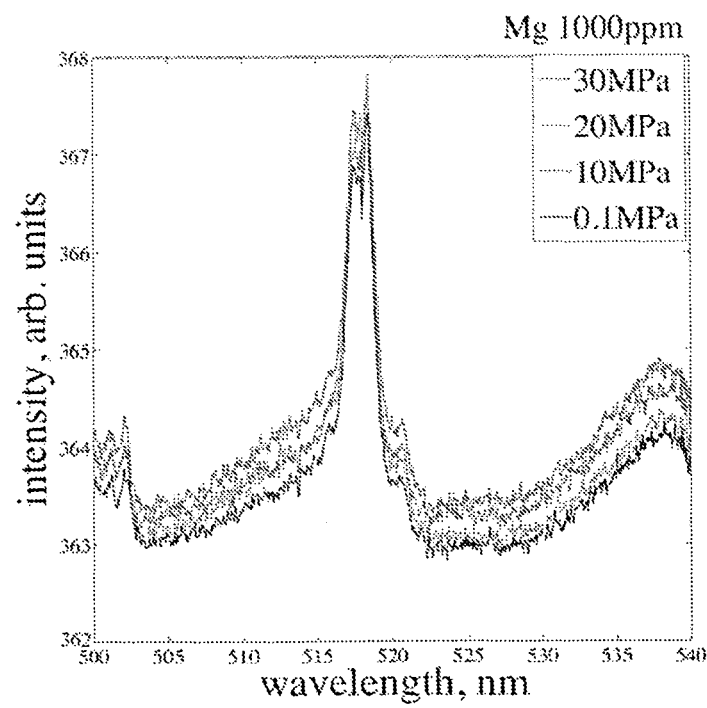
FIG. 18B is a view illustrating LIBS signals of dissolved magnesium in liquid at 0.1 MPa, 10 MPa, 20 MPa, and 30 MPa.
Figure 18C:
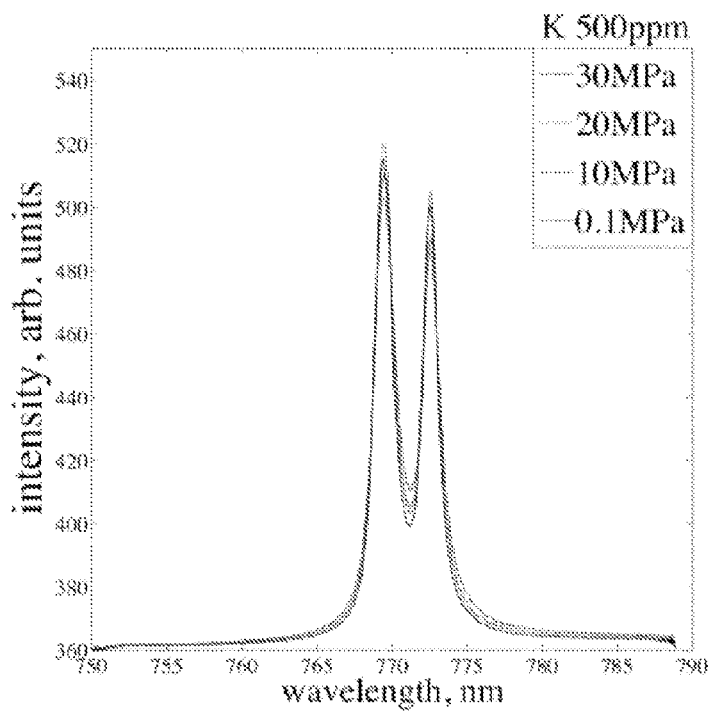
FIG. 18C is a view illustrating LIBS signals of dissolved potassium in liquid at 0.1 MPa, 10 MPa, 20 MPa, and 30 MPa.
Figure 18D:
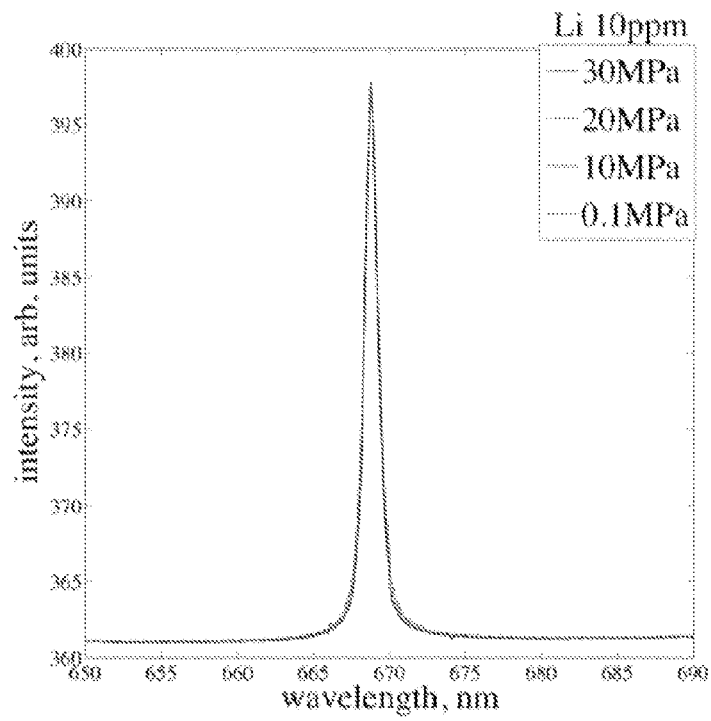
FIG. 18D is a view illustrating LIBS signals of dissolved lithium in the liquid at 0.1 MPa, 10 MPa, 20 MPa, and 30 MPa.
Figure 18E:
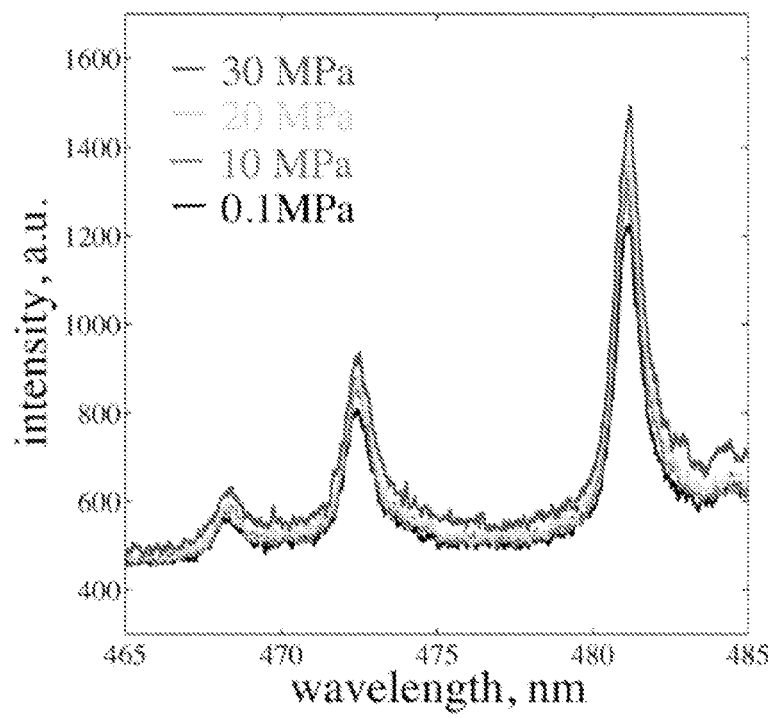
FIG. 18E is a view illustrating LIBS signals of solid zinc submerged in liquid at 0.1 MPa, 10 MPa, 20 MPa, and 30 MPa.
Figure 18F:
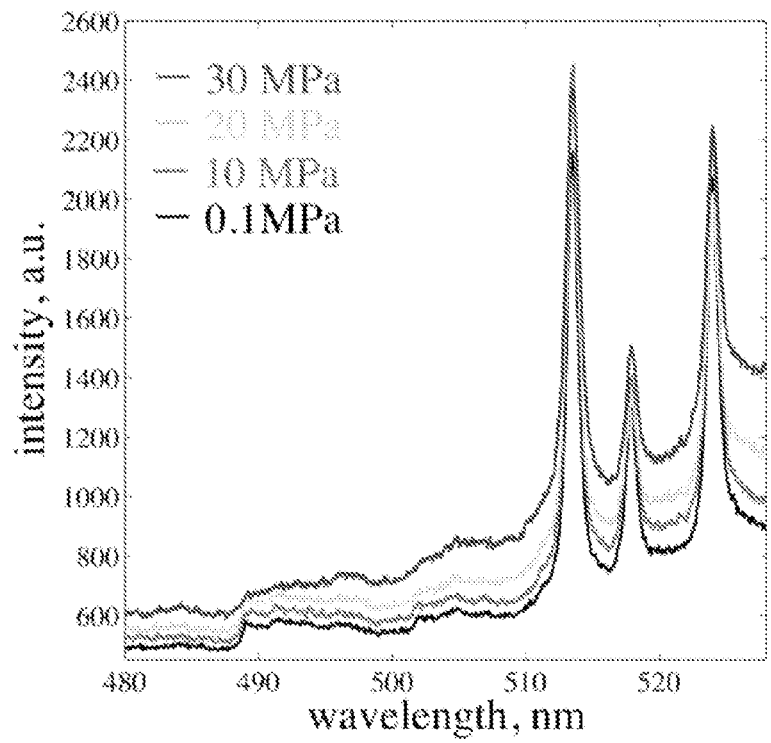
FIG. 18F is a view illustrating LIBS signals of solid copper submerged in liquid at 0.1 MPa, 10 MPa, 20 MPa, and 30 MPa.
Figure 18G:
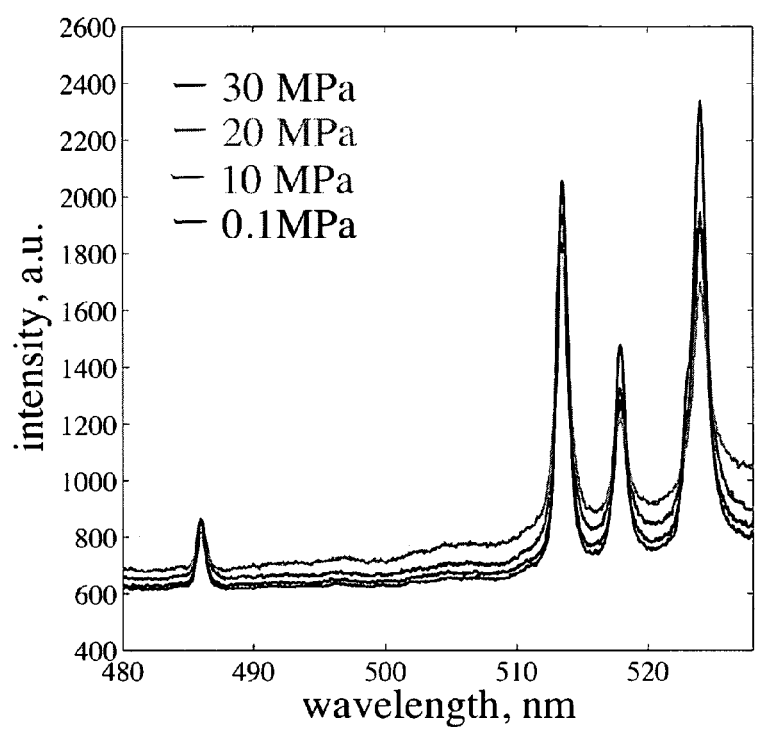
FIG. 18G is a view illustrating LIBS signals of solid brass submerged in liquid at 0.1 MPa, 10 MPa, 20 MPa, and 30 MPa.

FIGS. 18A to 18E illustrate LIBS signals of high-pressure liquid material and solid material in the high-pressure liquid using a single pulse laser. FIG. 18A illustrates LIBS signals of dissolved calcium in the liquid at 0.1 MPa, 10 MPa, 20 MPa, and 30 MPa. FIG. 18B illustrates LIBS signals of dissolved magnesium in the liquid at 0.1 MPa, 10 MPa, 20 MPa, and 30 MPa. FIG. 18C illustrates LIBS signals of dissolved potassium in the liquid at 0.1 MPa, 10 MPa, 20 MPa, and 30 MPa. FIG. 18D illustrates LIBS signals of dissolved lithium in the liquid at 0.1 MPa, 10 MPa, 20 MPa, and 30 MPa. FIG. 18E illustrates LIBS signals of solid zinc submerged in the liquid at 0.1 MPa, 10 MPa, 20 MPa, and 30 MPa. FIG. 18F illustrates LIBS signals of solid copper submerged in the liquid at 0.1 MPa, 10 MPa, 20 MPa, and 30 MPa. FIG. 18G illustrates LIBS signals of solid brass (zinc 35% and copper 65%) submerged in the liquid at 0.1 MPa, 10 MPa, 20 MPa, and 30 MPa. Such a single pulse has a feature that large signal variation is prevented from being caused by external pressure.

FIG. 4 described above illustrates LIBS signals of brass in the high-pressure liquid at 0.1 MPa and 30 MPa using a long pulse laser. The long pulse provides features that large signal variation caused by external pressure is suppressed and, especially for solid material in liquid, a peak of the LIBS signal is narrow compared to the single pulse.

FIGS. 5A to 5C described above illustrate LIBS signals of brass in the high-pressure liquid at 0.1 MPa, 2 MPa, and 5 MPa using double pulse lasers. Here, there is provided a feature that the LIBS signal at low pressure is strong and a peak thereof is narrow compared to the single pulse. Signal intensity is lowered with pressure increasing. However, satisfactory signal can be obtained with the single pulse by 5 MPa.

The examples described above can be modified variously based on technical idea of the present invention.

Industrial Applicability

Regarding the present invention, practical prototypes have been already prepared and effectiveness thereof has been verified in real sea. According to the present invention, it can be expected to drastically improve efficiency of investigation in underwater environment such as sea bed mineral resource survey and academic research. Further, to enable analysis of solid material at an elemental level in water or wet conditions, it is considerable that the present invention is applied to environment pollution investigation in the atmosphere, examination of a state of an inner wall of a pipeline for liquid transfer, observation of a pit inside, and verification of material at a factory production line. Further, since measurement can be performed without setting a device main body to be close to a target owing to that a signal is transmitted through a fiber, it is considerable that the present invention is applied in ultimate environment such as being inside of an atomic reactor. Specific study thereof has been in progress.

EXPLANATION OF REFERENCES

1 Pulse laser
2 Laser controller
3 Timing signal generator
4 Spectroscope
5 ICCD camera
6 Computer
7 Half mirror
8 Collecting lens
9 Window
10 Sample
11 Incident lens
12a, 12b Pressure-resistant container
13 First pressureproof-feedthrough-equipped fiber
15 Collimation mirror
16 Collecting mirror
17 Spherical window
18 Elliptic mirror
19 Dichroic mirror
20 Spectroscope optical fiber
21 Long pulse laser
22 Focusing stage
23 Filtrated water supplying portion
24 Robot arm
25 Reflection light
26 Radius r1
27 Radius r2
28 Lens system
29 Pressure-resistant window and lens
30 Collimation lens
31 Cassegrain optical system
32 Pressureproof-feedthrough-equipped fiber bundle
33 Collecting mirror
34 Spectroscope-side sleeve
35 Optical-head-side sleeve
38 Reflection mirror
39 Borehole
40 Deposition substance
41 First pulse laser
42 Second pulse laser
43 Half-wavelength plate
44 Reflection mirror
45 Polarization beam splitter
46 Partial-reflection mirror
47 Camera
48 Laser control cable
49 Small laser
50 Laser beam expander
60 Optical head
70 Optical head
71a, 71b Fiber pressureproof feedthrough
72 Second pressureproof-feedthrough-equipped fiber

The invention claimed is:

1. A chemical analysis device to analyze a chemical composition of a sample, comprising:
   a main body that includes a laser light source, a chemical analysis unit, and a housing that houses the laser light source and the chemical analysis unit as having a pressure-resistant function;
   an optical head that is arranged to be faced to the sample; and
   a pressureproof-feedthrough-equipped fiber that is extended from the housing to the optical head to guide laser light emitted from the laser light source to the optical head,
   wherein the optical head includes a minor system that causes the sample to be irradiated with laser light outgoing from the pressureproof-feedthrough-equipped fiber and to cause plasma emission light occurring at the sample owing to irradiation with the laser light to reenter to the pressureproof-feedthrough-equipped fiber,
   the chemical analysis unit performs spectroscopic analysis on the plasma emission light that reentered to the pressureproof-feedthrough-equipped fiber,
   the optical head further includes a liquid discharging unit to clean a vicinity of the sample, and
   the liquid discharging unit includes a pump that draws liquid at the outside of the optical head, a filter that generates filtrated water by eliminating impurities from the liquid drawn by the pump, and a discharging portion that discharges the filtrated water generated by the filter to the vicinity of the sample.

2. The chemical analysis device according to claim 1, wherein the pressureproof-feedthrough-equipped fiber includes a single optical fiber and bundle fibers arranged around the single optical fiber.

3. The chemical analysis device according to claim 1, wherein the laser light source emits long pulse laser light with an emission time being in a range of 200 to 400 nsec.

4. The chemical analysis device according to claim 1, wherein the optical head includes a window through which the laser light passes and LIBS signal light formed of the plasma emission light passes, and
   the window includes each part of two spherical faces of concentric spheres or each part of two faces having a center being close to concentric spheres as an incident face and an outgoing face of light.

5. The chemical analysis device according to claim 1, further comprising a control mechanism that causes the optical head to move for focusing the laser light on the sample.

6. The chemical analysis device according to claim 1, wherein the optical head includes a Cassegrain optical system.

* * * * *